United States Patent
Atzler et al.

(10) Patent No.: US 12,024,696 B2
(45) Date of Patent: Jul. 2, 2024

(54) SYSTEM AND METHOD FOR ORGANOID CULTURE

(71) Applicant: Molecular Devices (Austria) GmbH, Wals (AT)

(72) Inventors: Josef Atzler, Hallein (AT); Andreas Kenda, Klagenfurt (AT); Felix Spira, Strasswalchen (AT); Oksana Sirenko, San Carlos, CA (US)

(73) Assignee: Molecular Devices (Austria) GmbH (AT)

( * ) Notice: Subject to any disclaimer, the term of this patent is extended or adjusted under 35 U.S.C. 154(b) by 1222 days.

(21) Appl. No.: 16/407,026

(22) Filed: May 8, 2019

(65) Prior Publication Data

US 2020/0354660 A1 Nov. 12, 2020

(51) Int. Cl.
| | |
|---|---|
| C12M 3/00 | (2006.01) |
| C12M 1/00 | (2006.01) |
| C12M 1/12 | (2006.01) |
| C12M 1/34 | (2006.01) |
| C12N 5/00 | (2006.01) |

(52) U.S. Cl.
CPC ............ *C12M 21/08* (2013.01); *C12M 23/22* (2013.01); *C12M 25/14* (2013.01); *C12M 41/46* (2013.01); *C12N 5/0062* (2013.01); *C12N 2513/00* (2013.01)

(58) Field of Classification Search
CPC ...... C12M 23/58; C12M 21/08; C12M 41/46; C12M 25/14; C12M 41/36; C12M 23/22; C12M 29/04; C12M 35/08; C12M 23/34; C12N 5/0062; C12N 2513/00; C12N 2533/12; C12N 5/0075
See application file for complete search history.

(56) References Cited

U.S. PATENT DOCUMENTS

| | | | | |
|---|---|---|---|---|
| 5,409,829 A * | 4/1995 | Mussi | .................... | C12M 25/04 435/396 |
| 2010/0075417 A1* | 3/2010 | Cohen | .................. | C12N 5/0606 435/325 |
| 2011/0281351 A1* | 11/2011 | Adachi | ............... | A61L 27/3895 435/395 |

FOREIGN PATENT DOCUMENTS

| | | |
|---|---|---|
| EP | 3112450 | 1/2017 |
| WO | 2017/175236 | 10/2017 |
| WO | 2017/216113 | 12/2017 |

OTHER PUBLICATIONS

Iwashiro et al. Connective Tissue Research, 2011, 52(4):340-352.*
Tamai et al. Tissue Engineering: Part A, 2013, 19(21-22):2527-2535.*
Ong (Pediatric Research, 2018, 83(1):223-231.*
Sonntag (Proc. Of SPIE, 2016, 9705, 1-12.*
Balakrishnan, Sreenath et al., "A scalable perfusion culture system with miniature peristaltic pumps for live-cell imaging assays with provision for microfabricated scaffolds", Bioresearch Open Access, vol. 4, No. 1, Dec. 1, 2015, pp. 343-357.
Beckwith et al., "Monolithic, 3D-printed microfluidic platform for recapitulation of dynamic tumor microenvironments", Journal of Microelectromechanical Systems, IEEE Service Center, US, vol. 27, No. 6, Dec. 1, 2018, pp. 1009-1022.
Lerman, Max et al., "3D printing in cell culture systems and medical applications", Applied Physics Reviews, American Institute of Physics, vol. 5, No. 4, Dec. 18, 2018, pgs.
Ong et al., "A 3D printed microfluidic perfusion device for multicellular spheroid cultures", Biofabrication, vol. 9, No. 4, Sep. 11, 2017, pages.
PCT International Preliminary Report on Patentability in International Application PCT/IB2020/054357, dated Nov. 18, 2021, 9 pages.
PCT International Search Report and Written Opinion in International Application PCT/IB2020/054357, dated Aug. 7, 2020, 12 pages.

* cited by examiner

*Primary Examiner* — Sean C. Barron
(74) *Attorney, Agent, or Firm* — Merchant & Gould P.C.

(57) ABSTRACT

The present disclosure provides a system, including methods and apparatus, for culturing, monitoring, and/or analyzing organoids. In an exemplary method of organoid culture, the method may comprise disposing a scaffold in a receptacle having an open side. A sealing member may be bonded to the open side of the receptacle to create a chamber. An organoid may be formed in the chamber using the scaffold. Fluid and/or at least one substance may be introduced into the chamber from an overlying reservoir for contact with the organoid.

7 Claims, 22 Drawing Sheets

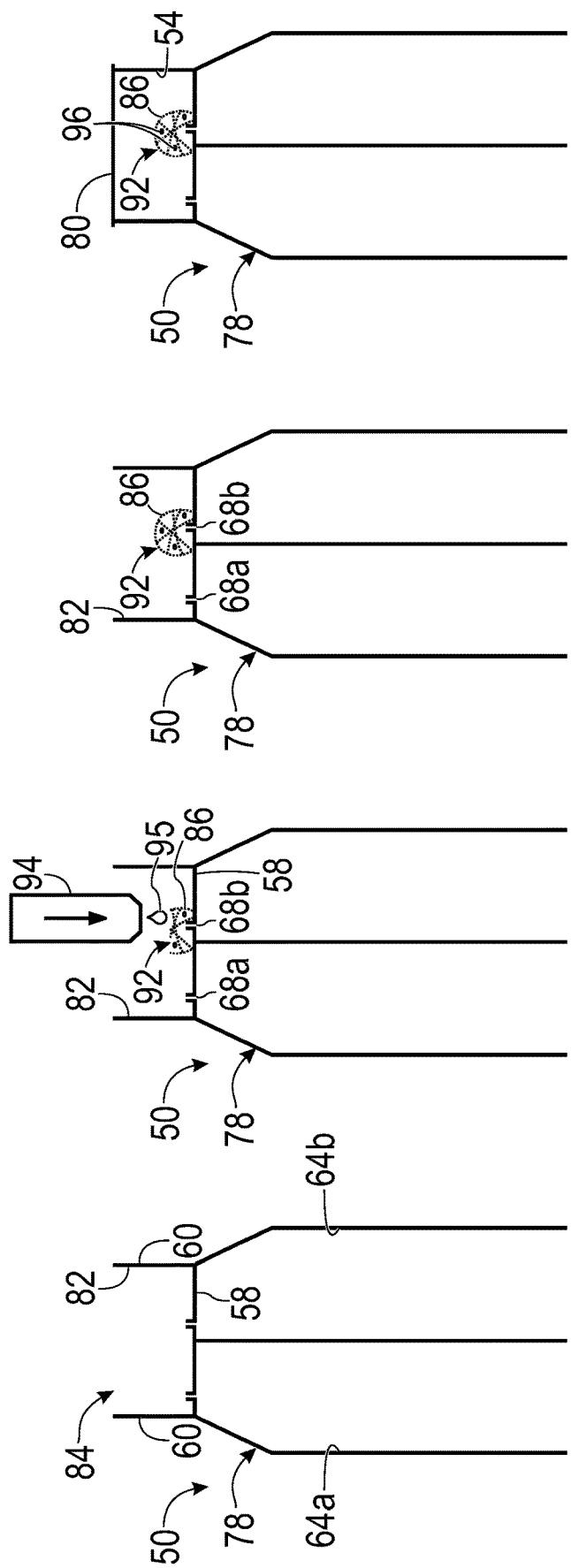

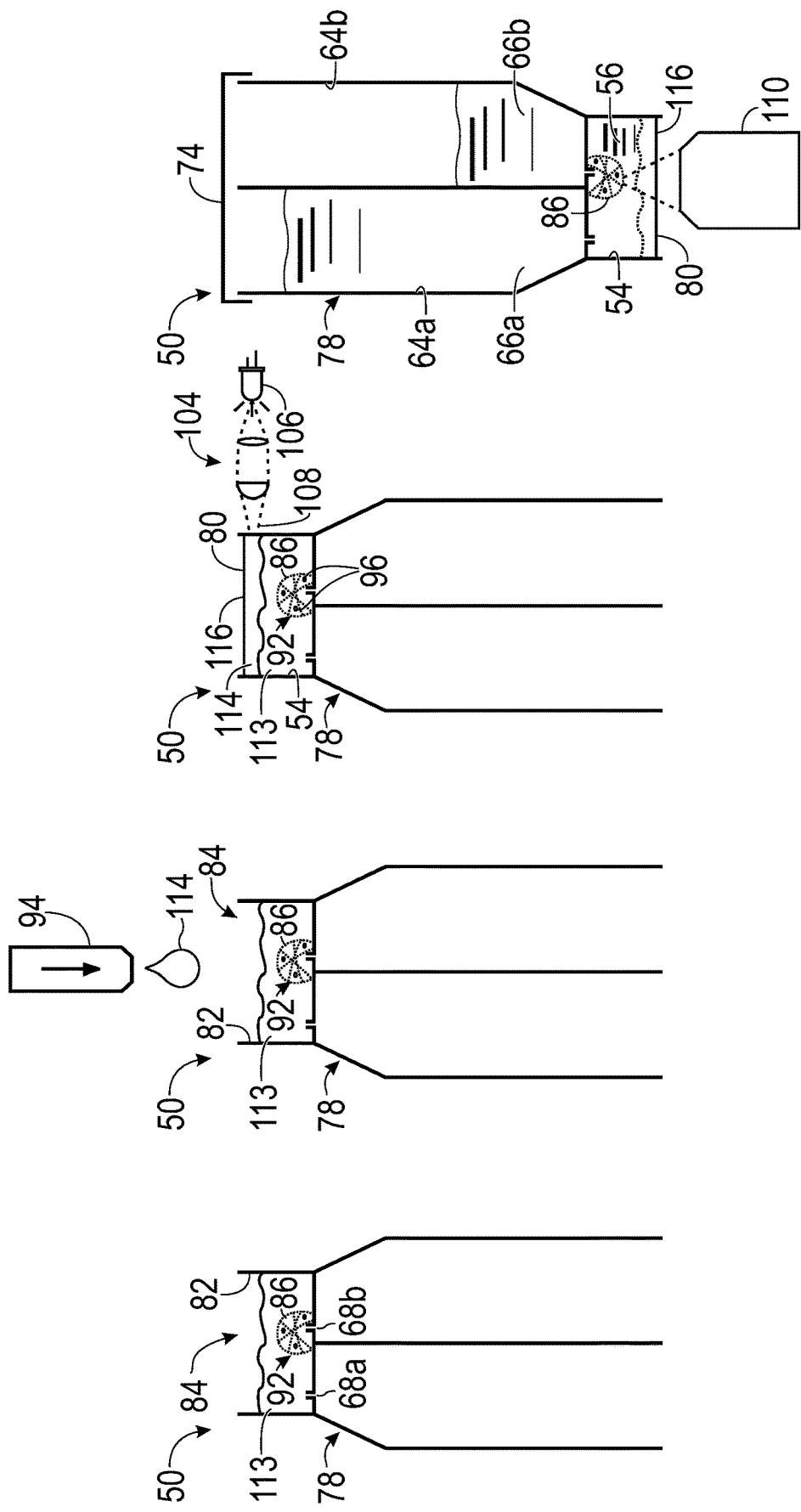

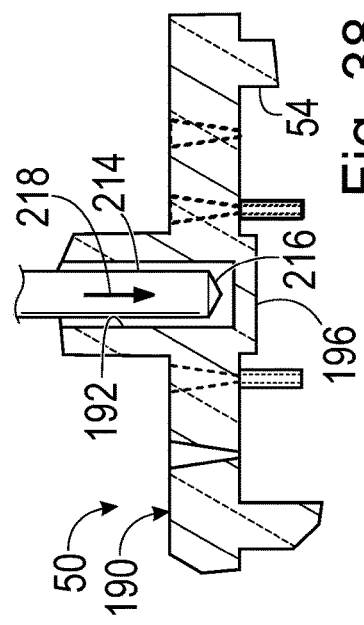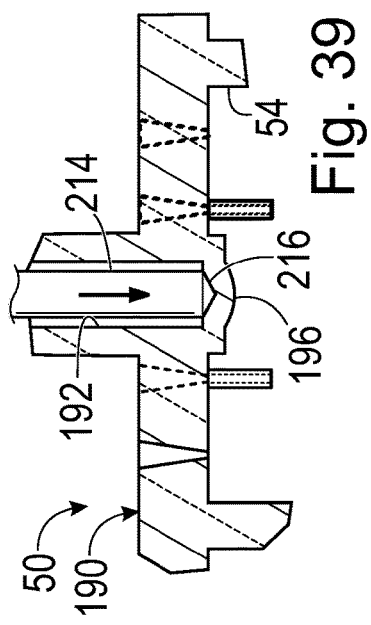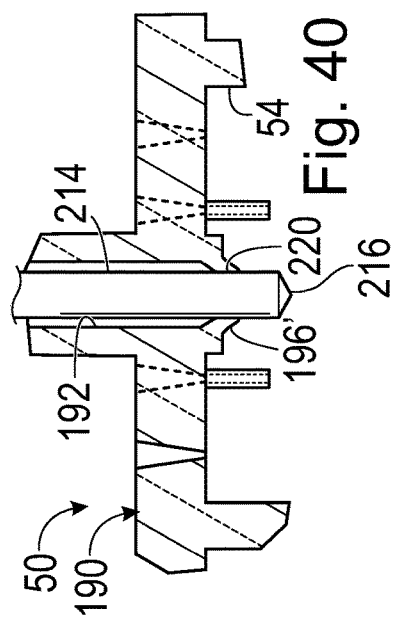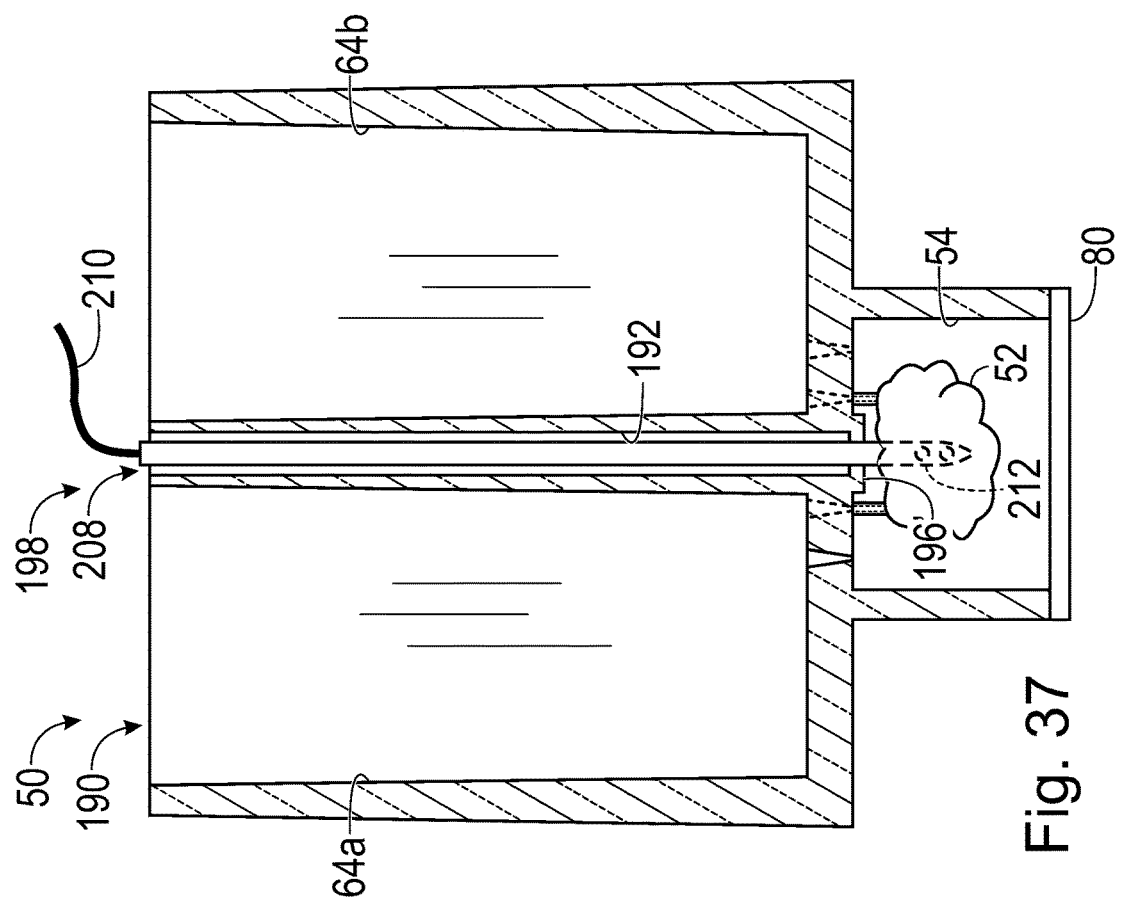

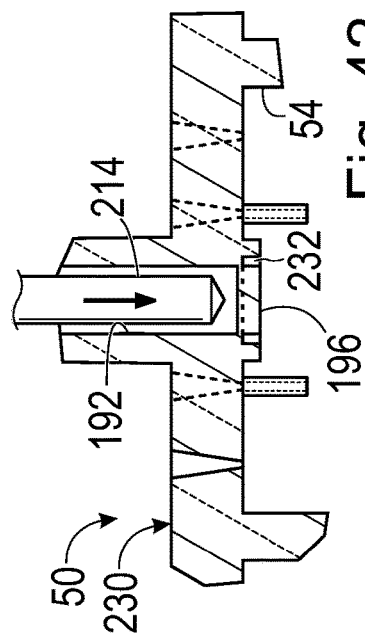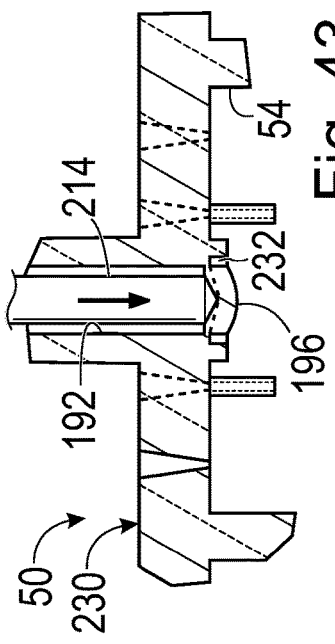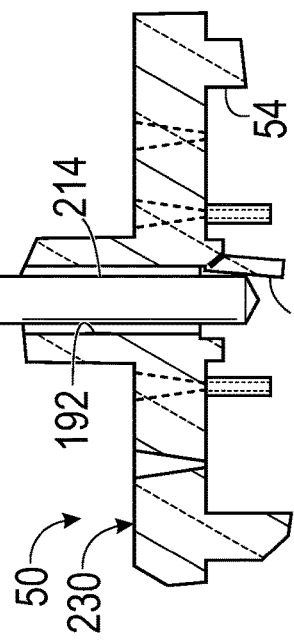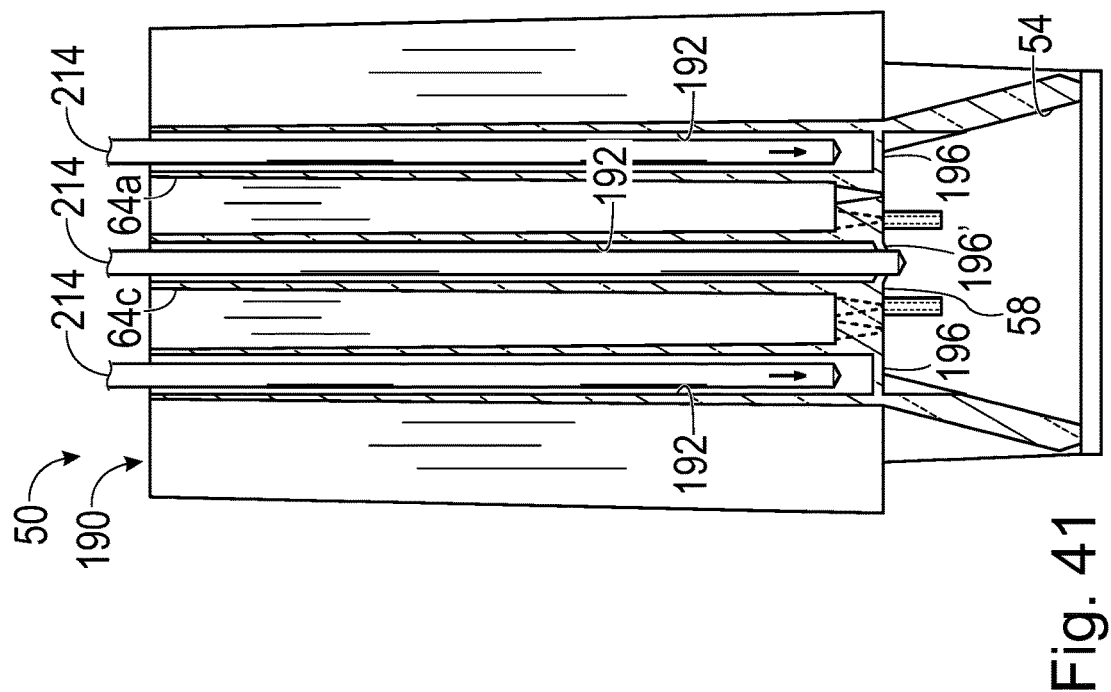

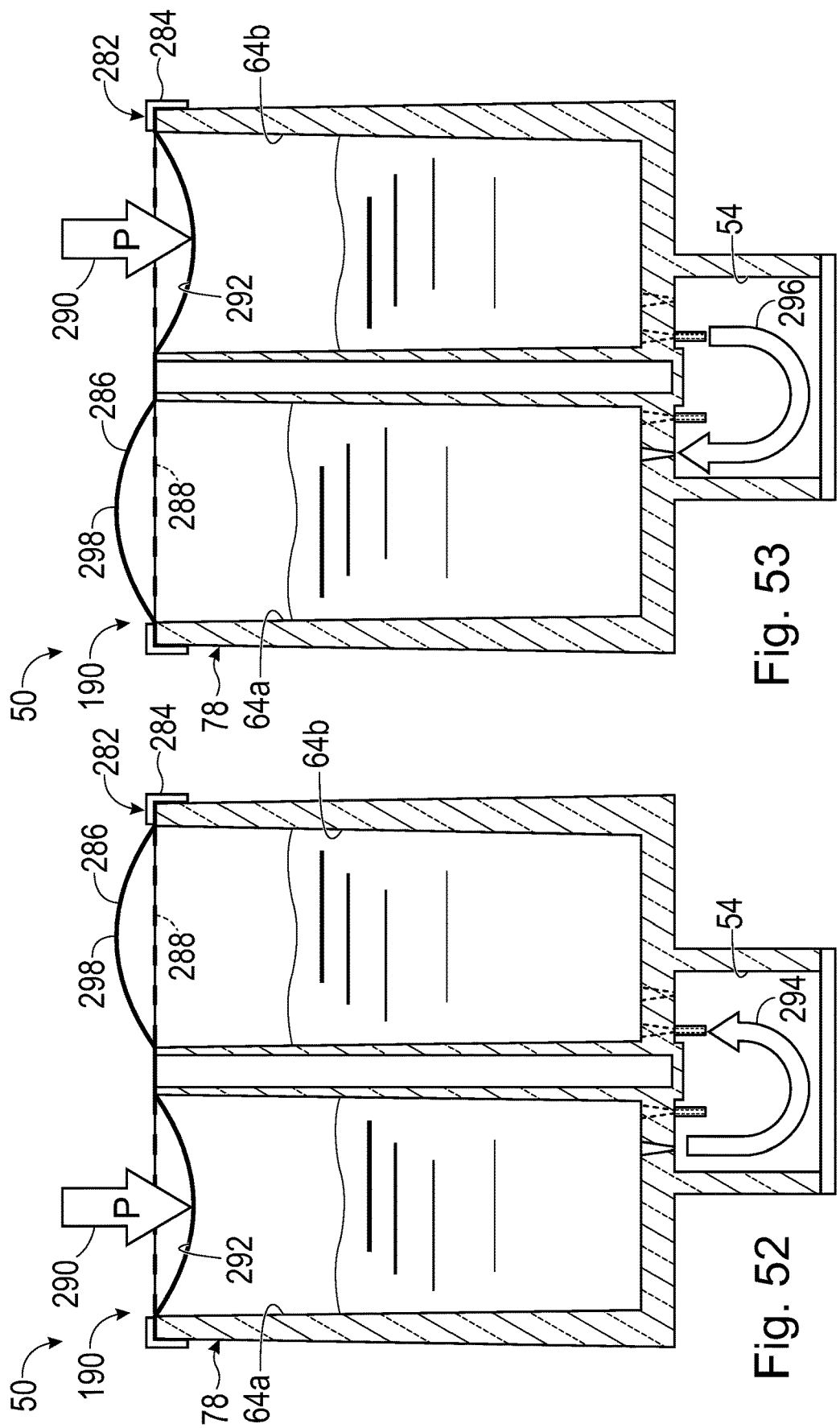

SYSTEM AND METHOD FOR ORGANOID CULTURE

INTRODUCTION

An organoid (a "mini-organ") is a three-dimensional mass of cells of different types produced in vitro and having some resemblance to an organ, such as exhibiting a realistic histology of organ-specific tissue. The mass of cells can be generated by seeding a matrix with a small number of stem cells. The stem cells then proliferate, differentiate, and self-organize within the matrix, while using the matrix as a scaffold. With this approach, organoids resembling tissue from the brain, heart, intestine, kidney, liver, and stomach, among others, have been generated so far. These promising results suggest that organoid culture has the potential to provide new insights into organ development and function, and to recapitulate disease models that allow drug screening in vitro. Organoids may revolutionize how drugs are discovered and medicine is personalized.

There are a number of problems that limit the ability of researchers to exploit organoids fully. First, as organoids increase in size, they may need to be fed from both the inside and the outside, which presents a challenge. Second, each different type of organoid can require an optimized three-dimensional matrix scaffold structure, media exchange (feeding) appropriate for that structure, and possibly even the ability to experience mechanical resistance or controlled force, to allow proper growth and development of a functioning organoid. Third, there are no vessels optimized for exposing large organoids to different types of reagents to allow screening. Fourth, there are no vessels optimized for monitoring large organoids in situ by imaging methods. Instead, organoids are often imaged after they have been fixed and sectioned physically. Accordingly, systems and methods are needed for improving organoid culture, such as by providing the ability to efficiently grow, monitor, and analyze large organoids.

SUMMARY

The present disclosure provides a system, including methods and apparatus, for culturing, monitoring, and/or analyzing organoids or other organized multi-cellular structures. In an exemplary method of organoid culture, the method may comprise disposing a scaffold in a receptacle having an open side. A sealing member may be bonded to the open side of the receptacle to create a chamber. An organoid may be formed in the chamber using the scaffold. Fluid and/or at least one substance may be introduced into the chamber from an overlying reservoir for contact with the organoid.

BRIEF DESCRIPTION OF THE DRAWINGS

FIG. 3 is a side view of a body of the vessel of FIG. 2, taken in isolation and inverted with respect to FIG. 2 before performance of a method of culturing, monitoring, and/or analyzing an organoid in the vessel, as illustrated in FIGS. 4-10.

FIGS. 4 and 5 are side views of the vessel body of FIG. 3, taken respectively during and after creation of a scaffold in a receptacle of the vessel by 3D printing or pipetting.

FIG. 6 is a side view of the vessel body of FIG. 5, taken after a pre-made sealing member has been bonded to the vessel body to seal an open side of the receptacle to produce a chamber containing the scaffold.

FIGS. 11-13 are side views of the vessel body and scaffold of FIG. 5 illustrating an alternative approach to sealing an open side of the receptacle of the vessel body to produce a chamber, by forming a sealing member in situ in the receptacle.

FIG. 14 is a side view of the vessel body, sealing member, and scaffold of FIG. 13 taken in the presence of an imaging objective, and after the vessel body has been flipped over to an organoid-culturing orientation, at least one liquid medium has been introduced into the chamber containing the scaffold and into overlying reservoirs in fluid communication with the chamber, and a lid of the vessel has covered the open tops of the reservoirs.

FIG. 37 is a sectional view of the vessel body and sealing member of FIG. 35, taken with an organoid present in the chamber and with the magnet replaced by a sensor/electrode having a sensing/stimulating end region that has pierced the breachable barrier and entered the organoid.

FIGS. 38-40 are fragmentary sectional views of the vessel body of FIG. 35, taken around the breachable barrier before, during, and after a tip of a breaching instrument passes through the barrier and into the chamber from the access tube.

FIG. 41 is a sectional view of the vessel body and sealing member of FIG. 35, taken generally as in FIG. 24 (for a related embodiment), such that three access tubes are visible, with breaching instruments disposed in the three access tubes, and with only one of breaching instruments extending into the chamber below the access tubes.

FIGS. 42-44 are fragmentary sectional views of a modified embodiment of the vessel body of FIG. 35 in which the breachable barrier is configured to tear at a frangible web, with the views taken around the breachable barrier before, during, and after the tip of a breaching instrument passes through the breachable barrier from the access tube.

FIGS. 52 and 53 are sectional views of the vessel body and sealing member of FIG. 35, taken with a cap mounted to and hermetically sealing the top of the vessel body and providing a flexible member(s) that is being deformed by external pressure applied alternately over a pair of reservoirs to drive liquid through the chamber alternately in opposite directions.

DETAILED DESCRIPTION

Figure 1:
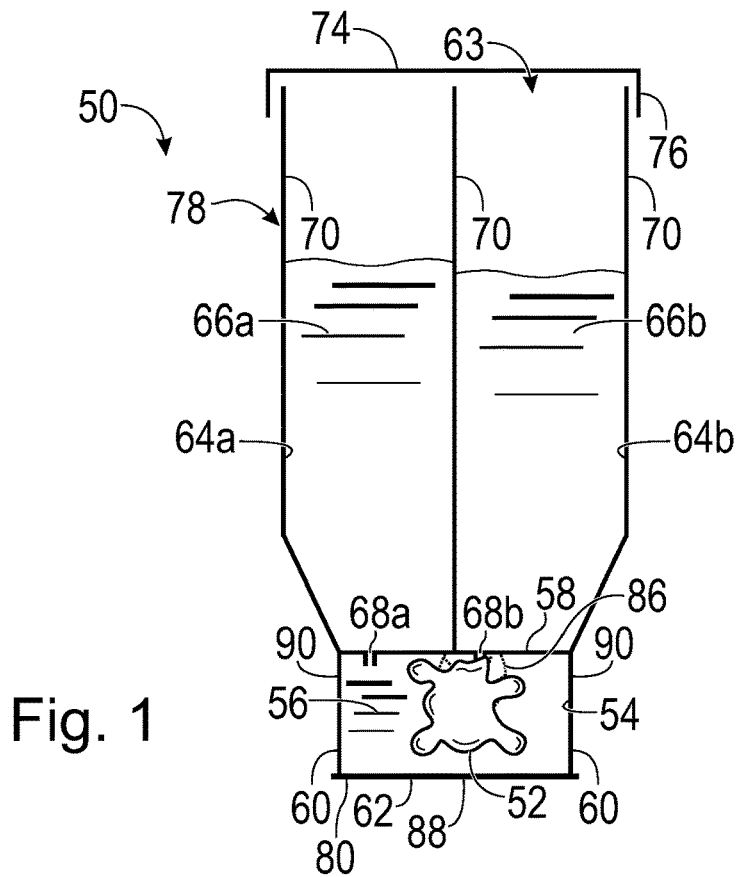
FIG. 1 is a schematic side view of an exemplary vessel for forming, culturing, monitoring, and analyzing an organoid, taken with the vessel holding an organoid submerged in a liquid culture medium, and with front and back walls of the vessel not visible.

The present disclosure provides a system, including methods and apparatus, for culturing, monitoring, and/or analyzing organoids or other organized multi-cellular structures, such as developing or fully-developed multi-cellular organisms, tissue biopsies, and/or primary patient material, among others. In an exemplary method of organoid culture, the method may comprise disposing a scaffold in a receptacle having an open side. A sealing member may be bonded to the open side of the receptacle to create a chamber. An organoid may be formed in the chamber using the scaffold. Fluid and/or at least one substance may be introduced into the chamber from an overlying reservoir for contact with the organoid.

The present disclosure describes a vessel for formation, culture, monitoring, and/or analysis of organoids or other organized multi-cellular structures, such as developing or fully developed multi-cellular organisms, tissue biopsies, and/or primary patient material, among others. The vessel may be consumable (i.e., disposable after a single use) and/or may have a standard shape. The vessel may include a vessel body defining a receptacle having an open side. A sealing member may be attached (e.g., bonded) to the vessel body to form a chamber from the receptacle. The sealing member may be pre-formed or formed in the receptacle, among others.

A three-dimensional (3D) structure (i.e., at least one matrix, which may be a scaffold) may be disposed in the receptacle before the open side thereof is sealed. The 3D structure may be formed in the receptacle by a 3D printer. The 3D printer may dispense one or more solidifiable bioinks that may be mixed with cells before or as the ink(s) is deposited to generate the 3D structure. Alternatively, the cells may be introduced into the receptacle or chamber separately from the 3D structure. In other embodiments, the 3D structure may be formed at least partially or completely outside the receptacle and then disposed therein.

Suitable cells that may be introduced into the matrix scaffold as it is being created or after it has been created may include non-differentiated stem cells, stem cells that have already differentiated and will continue to differentiate, cell aggregates, small organoids, and/or the like.

The 3D printer also may be utilized to apply adhesive and/or sealing fluid to the vessel body to allow sealing of the open side of the receptacle with a transparent sealing member at the end of the printing process. Exemplary printing techniques that may be suitable for dispensing matrix components include droplet-based bioprinting using a bioink(s), or laser-based bioprinting (e.g., laser-based direct-writing to print cells, enzymes, etc., by laser-induced forward transfer (LIFT) with a pulsed laser).

The scaffold and/or other matrix may be provided by one or more hydrogels. Each hydrogel may include one or more thermoplastic structural components, such as Matrigel, alginate, nanofibrillar cellulose, collagen, fibrin, and/or polyethylene glycol, among others, that cooperatively form a matrix in a temperature-dependent fashion.

In some embodiments, two or more different hydrogels/matrices may be disposed in a receptacle. The hydrogels/matrices may differ for any suitable parameters, such as melting temperature, resistance to enzyme degradation, solubility, cell-attraction and/or cell-repulsion characteristics, and/or the like.

Each hydrogel/matrix may include any suitable components. Exemplary components include one or more polysaccharides (e.g., glycosaminoglycans (GAGs, such as chondroitin sulfate, dermatan sulfate, heparin, heparan sulfate, hyaluronic acid, keratan sulfate, etc.), proteoglycans (e.g., GAGs linked to a core protein (such as via serines thereof) to form aggrecan, agrin, brevican, collagen type XVIII, leprecan, neurocan, perlecan, small leucine-rich proteoglycans, versican, or the like), fibrous proteins (e.g., collagen, elastin, fibronectin, laminin, etc.), and/or the like. Protease recognition sites (e.g., for a scaffold metalloproteinase (MMP)) may be incorporated into the hydrogel/matrix to allow degradation/remodeling by cells. The frequency of such sites, along with the sequence of each site may be selected to permit a suitable amount of degradation/remodeling.

One or more growth factors may be included in the matrix when formed, or may be introduced in a liquid medium after formation. Exemplary growth factors that may be suitable include angiopoietin, bone morphogenetic proteins (BMPs), ciliary neurotropic factor, colony stimulating factors, ephrins, epidermal growth factor, erythropoietin, fibroblast growth factors, glial-derived neurotrophic factor, hepatocyte growth factor, insulin, insulin-like growth factors, interleukins, leukemia inhibitory factor, keratinocyte growth factor, neuregulins, neurotrophins, platelet-derived growth factor, transforming growth factors, tumor necrosis factor (alpha), vascular endothelial growth factor, and/or the like.

Any suitable cells may populate the scaffold initially. These cells may include stem cells (e.g., pluripotent stem cells), support cells, and/or the like. The cells may be deposited in a scaffold by any suitable technique including bioink droplet printing, micro-contact printing, photolithography, dip pen nanolithography, and/or pipetting, among others.

The vessel may provide a plurality of reservoirs that are in fluid communication with the chamber via channels, which may be formed in shared wall(s) between the reservoirs and the chamber. This configuration may be described as a standard feeding interface. In some embodiments, 3D printing provides connection of the standard feeding interface inside the vessel to any suitable printed structure to enable the growth of different types of organoids.

The printed 3D structure can provide temporary scaffolding for cells of the appropriate type(s) as they develop into an organoid. The cells may self-organize and produce their own extracellular matrix, which may replace some or all of the scaffolding. The same may be true for internal feeding—the vessel may provide a general interface, which optionally may be modified by 3D printing, and the cells may organize to best use this modified interface.

The scaffold (with or without cells) may be disposed in the receptacle of the vessel body, and the chamber may be formed from the receptacle, while the vessel is upside down. Once these processes are completed, the vessel may be turned right-side up (to its organoid-culturing orientation), and at least one reservoir overlying the chamber may be filled with feeding liquid. If there are not yet any cells inside the scaffold, suitable cells may be placed into the feeding liquid and introduced into the scaffold together with the feeding liquid from an overlying reservoir (or cells may be introduced via an access tube (e.g., see Example 7)).

The forming organoid may need an initial incubation time before a specific feeding protocol can be started. The feeding protocol may involve loading reservoirs with suitable media and removing media from the reservoirs according to a predefined schedule and/or based on the developmental stage or condition of the organoid. The feeding protocol may depend on the shape of the scaffold as well the type of organoid that is to be formed.

The vessel may be structured to enable organoid monitoring via a bottom window of the chamber, which may be provided by the sealing member. In some embodiments, the organoid may be monitored while remaining inside an incubator. Accordingly, the incubator may include an imaging system for organoid monitoring.

The vessel may enable light-sheet 3D imaging. The chamber of the vessel may have two, three, or more optical windows, and light may propagate into and/or out of the chamber via each window. For example, the vessel may have a bottom window and one or more lateral windows, each of which may be planar. In some embodiments, the vessel may have a pair of lateral windows arranged opposite one another.

A plurality of vessel bodies (and vessels) may be organized as a strip. The strip may be created by pre-attaching vessel bodies to one another in a linear or two-dimensional array during manufacture (e.g., by bonding or forming the vessel bodies integrally with one another, such as by injection molding). Alternatively, the strip may be created during manufacture or by the user by assembling individual vessel bodies with a suitable strip holder. In some embodiments, the strip holder may be configured to hold only one strip or two strips to allow room for imaging objectives. A strip of vessel bodies may be loaded into a 3D printer, to allow the printer to print a scaffold in and/or add a sealing member to each of the vessel bodies.

The present disclosure enables generation of large functional organoids by feeding the organoids with different media inside and outside. The large organoids may be greater than about 0.1, 0.2, 0.5, 1, or 2 millimeters, among others, in average diameter or maximum diameter. Working with large organoids is still challenging and researchers are facing two major limitations. First, each type of organoid needs different culture conditions like specific hydrogels, matrices as a substrate, or even mechanical properties like shear force by media flow. Second, microscopy of large organoids is very challenging. State-of-the-art methods are still thin-sectioning of the organoid material, staining, and image acquisition of fixed samples using confocal point scanning microscopes or even slide readers.

The present disclosure offers systems and methods to facilitate overcoming one or both obstacles. By using a combination of 3D printing (scaffold and/or cells) together with media exchange by gravity flow, the user may generate a unique 3D environment that is optimized for each type of organoid. A wide range of different organoid types may be grown. Feeding and waste removal may be addressed by fluid communication between the vessel's chamber and overlying reservoirs. Integrating optical windows into each vessel, at least one for entry of excitation light, and another for exit of emitted light, allows monitoring living cells of the organoid by light-sheet microscopy. Alternatively, or in addition, the organoid may be imaged by classical widefield microscopy via one or more of the windows. Thus, the vessel disclosed herein may enable performance of live cell microscopy of a developing and/or developed organoid. High-content and/or high-throughput microscopy may be performed on organoids.

Further aspects of the present disclosure are described in the following sections: (I) vessel for organoid formation, culture, monitoring, and/or analysis, (II) methods of organoid formation, culture, monitoring, and/or analysis, and (III) examples.

I. VESSEL FOR ORGANOID FORMATION, CULTURE, MONITORING, AND/OR ANALYSIS

Figure 2:
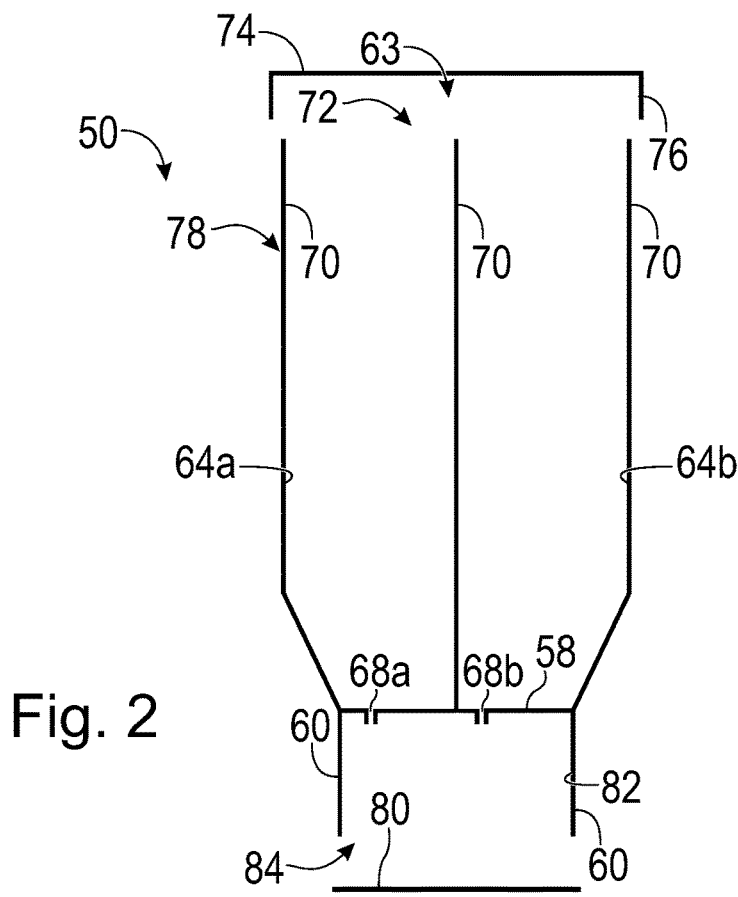
FIG. 2 is an exploded side view of the vessel of FIG. 1 taken while the vessel is empty.

This section describes an exemplary vessel 50 for formation, culture, monitoring, and/or analysis of an organoid 52 (or other organized multi-cellular structure); see FIGS. 1 and 2. Vessel 50 is shown schematically here, with front and back walls not visible, to distinguish top and bottom sides of the vessel that are closed (FIG. 1) or open (FIG. 2).

FIG. 1 shows vessel 50 containing organoid 52 in a chamber 54, with the organoid submerged in a medium 56 (e.g., a liquid or semi-solid culture medium to encourage organoid growth and development). Organoid 52 may be attached to an upper region of chamber 54, such as a top wall 58 thereof. (The top wall interchangeably is called a ceiling.) Lateral walls 60 and a bottom wall 62 of the chamber may provide barriers to passage fluid, thereby rendering all of the chamber below top wall 58 fluid-tight.

Vessel 50 defines a plurality of compartments 63 located over chamber 54. Each compartment 63 may share a wall with chamber 54 and may or may not be in fluid communication initially with the chamber. Exemplary compartments include reservoirs and access tubes (see Example 7). Here, vessel 50 includes (at least) two reservoirs 64a, 64b for holding a respective liquid medium 66a, 66b over chamber 54. Each reservoir 64a, 64b may be in fluid communication with chamber 54 independently of each other reservoir, via a corresponding, dedicated channel 68a, 68b. Each channel 68a, 68b may extend through top wall 58 from one of reservoirs 64a, 64b to chamber 54, and may be flush with the top and bottom sides of top wall 58, or may project from the top side and/or bottom side of top wall 58 as the lumen of an annular protrusion (e.g., see Example 4). In other examples, vessel 50 may have at least or exactly 3, 4, 5, 6, or more overlying reservoirs, each of which may be in fluid communication with chamber 54 through top wall 58, and/or independently of each other reservoir (e.g., see Example 3).

The two or more reservoirs of vessel 50 may hold any suitable substances to be supplied to chamber 54. Exemplary substances include nutrients, effectors, and reagents, among others. Suitable nutrients include any substances to facilitate the health and proliferation of cells, and thus growth and development of organoid 52, inside chamber 54. Exemplary nutrients may include sugars (such as glucose), amino acids, proteins, nucleotides, vitamins, minerals, fatty acids, etc. Effectors include any molecules (such as inducers or repressors) that activate, control, or inactivate a process or action (such as differentiation, protein synthesis, migration, etc.). Exemplary effectors include anti-cancer compounds, growth factors, differentiation factors, oligonucleotides, mRNAs, or the like. Reagents include any compounds that facilitate analysis of an organoid. Exemplary reagents include labels, fixation agents, and clearing agents, among others. The labels may include dyes (e.g., visible stains and/or photoluminescent dyes). Photoluminescent dyes are any substances that emit light in response to irradiation with excitation light.

Each reservoir 64a, 64b may have lateral walls 70 to contain fluid laterally. At least one lateral wall may be shared between at least one adjacent pair of the reservoirs, as depicted in FIG. 1. In other examples, at least one pair of reservoirs, of the same or different vessels, may be in fluid communication with one another laterally, independent of chamber(s) 54 (e.g., see Example 2), such as via a channel formed in a wall 70 shared between reservoirs.

Each reservoir 64a, 64b may have an open top 72 to facilitate introduction and removal of fluid with a fluid-transfer device (e.g., a pipet or other pump). Vessel 50 may include a single, removable lid 74 that fits over the vessel to cover open top 72 of each reservoir 64a, 64b during incubation in an incubator. Alternatively, the vessel may include two or more lids that are removable independently from one another and that collectively cover all of the reservoirs. Each lid 74 may have a flange 76 configured to vertically overlap the upper end of each reservoir and restrict lateral motion of the lid when covering the reservoir(s), optionally without creating a tight fit. In some embodiments, the lid may be cap that forms a fluid-tight seal at the top of one or more reservoirs (e.g., see Example 8).

FIG. 2 shows an exploded view of vessel 50 of FIG. 1 with the vessel empty. Vessel 50 may include lid 74, a vessel body 78, and a sealing member 80. Vessel body 78 may define reservoirs 64a, 64b and a receptacle 82 under the reservoirs. Receptacle 82 provides top wall 58 and lateral walls 60 of chamber 54. However, receptacle 82 may have an open bottom side 84 that can be sealed with a flat sealing member 80 to create chamber 54, after a scaffold 86 to support organoid formation has been disposed in receptacle 82 (see FIG. 1 and Section II). The sealing member can be bonded to a bottom end of receptacle 82 (and/or vessel body 78) to create chamber 54. In other embodiments, a sealing member can be formed in situ to seal bottom side 84 of receptacle 82 (see Section II).

Vessel 50 may have one or more optical windows to facilitate imaging (see FIG. 1). Each optical window may be used to propagate light into the chamber, to illuminate at least a portion of chamber 54, or to receive light from the chamber, such as for imaging. In exemplary embodiments, vessel 50 has a bottom window 88 provided by sealing member 80, and one or more lateral windows 90 provided by vessel body 78. Each optical window may be transparent and/or planar. Bottom window 88 may be transverse (e.g., orthogonal) to each lateral window 90, and the lateral windows may be formed by opposite lateral walls 60 of chamber 54. (The term "light," as used herein, means optical radiation, including ultraviolet radiation, visible radiation (i.e., visible light), and/or infrared radiation.)

The components of vessel 50 may be formed of any suitable material by any suitable procedures. In exemplary embodiments, vessel body 78 may be formed of polymer, such as transparent polymer. The vessel body may have no removable/moving parts and/or may be formed as a single piece, such as by injection molding, such that all of the structures (e.g., compartments) of the vessel body are formed integrally with one another. Accordingly, receptacle 82 (and/or chamber 54) and reservoirs 64a, 64b may have fixed positions relative to one another and/or may be non-removably/firmly attached to one another. Sealing member 80 may be formed of glass or polymer, among others, and may be pre-formed or formed in situ, at least partially or completely inside receptacle 82.

Chamber 54 (and/or receptacle 82) and each reservoir 64a, 64b may have any suitable size. Chamber 54 may have a volume of at least about 0.1, 0.2, 0.3, 0.4, 0.5, 0.7, or 1 mL. The chamber may be sized to contain an organoid of any suitable size (e.g., maximum size), such as an organoid having a diameter of at least about 0.2, 0.5, 1, 2, 3, 4, or 5 mm, among others. In exemplary embodiments, each overlying reservoir of the vessel is at least as large as, or about 2, 5, or 10 times the volume of chamber 54 (and/or receptacle 82), such as at least about 0.5, 1, 2, 4, or 6 mL, among others.

Vessel 50, and/or any of the compartments thereof, may have any suitable geometry. For example, each of receptacle 82, chamber 54, and/or each reservoir (e.g., reservoirs 64a, 64b) independently may have a polygonal (e.g., rectangular), elliptical (e.g., circular), ovoid, rosette, or other shape in cross-section (e.g., in a horizontal plane). Accordingly, receptacle 82, chamber 54, and/or each reservoir independently may be cylindrical, frustoconical, a rectangular prism, a tapered prism, or a combination thereof, among others.

Further aspects of vessel 50 that may be suitable for organoid formation, culture, monitoring, and/or analysis are described below.

II. METHODS OF ORGANOID FORMATION, CULTURE, MONITORING, AND/OR ANALYSIS

This section describes methods of forming, culturing, monitoring, and/or analyzing organoids (or other organized multi-cellular structures) in the vessels of the present disclosure; see FIGS. 3-15. The method steps described in the section may be performed in any suitable order and combination, using any of the vessels, vessel features, and/or procedures described elsewhere herein.

FIGS. 3-10 illustrate exemplary configurations of vessel 50, organoid 52, and media 56, 66a, 66b produced by performance of a method of organoid culture and analysis. At least one vessel body 78 of at least one vessel 50 may be selected for use. In some embodiments, a linear or two-dimensional array of vessel bodies 78 may be selected (e.g., see Examples 1 and 6), or the array may be created after at least a subset of the steps below have been performed.

FIG. 3 shows a vessel body 78 that has been selected and placed in an inverted orientation in which receptacle 82 is open on top. In other words, top wall 58 is positioned under open bottom side 84. This orientation takes advantage of gravity to encourage delivery of fluid onto top wall 58, while lateral walls 60 prevent lateral flow of fluid out of receptacle 82.

A scaffold 86 to be used for organoid formation may be disposed inside receptacle 82. The scaffold may be included in a hydrogel 92 that is created at least partially in situ, as shown in FIGS. 4 and 5. For example, scaffold 86 of hydrogel 92 may be printed in three-dimensions by a 3D printer 94 onto top wall 58. 3D printer 94 may utilize any suitable technology to deliver components of the scaffold. In some embodiments, the 3D printer may utilize inkjet technology, to deliver droplets of fluid (such as droplet 95), which may contain scaffold structural components, cells 96, tubes, caged effectors, growth factors, etc. Alternatively, or in addition, 3D printer 94 may utilize laser-induced forward transfer to deliver components (e.g., cells 96), among others. In other embodiments, at least part of scaffold 86 may be created separately from vessel body 78 and then placed into receptacle 82 (e.g., attached to top wall 58).

Hydrogel 92 may or may not be a thermoreversible gel. The hydrogel may have a gel point (a gelling temperature) above the culture temperature for the organoid, such that the scaffold of the hydrogel forms through cooling as the scaffold is being printed. Alternatively, or in addition, polymerization to form the hydrogel may be photo-induced with optical radiation, such as ultraviolet light or visible light, among others.

Scaffold 86 (and/or hydrogel 92) may horizontally overlap the bottom end of one or more channels 68a, 68b. For example, in the depicted embodiment, a through-axis (e.g., a vertical axis) defined by channel 68b intersects hydrogel 92 and extends through scaffold 86. In other embodiments, scaffold 86 (and/or hydrogel 92) may overlap a plurality of channels 68a, 68b.

One or more channels 68a, 68b may be extended by 3D printing during creation of scaffold 86 in hydrogel 92, to facilitate supplying nutrients and/or effectors to hydrogel 92 and cells 96 therein during organoid formation and culture. The resulting channel extensions may be one or more laterally-permeable tubes that are embedded in hydrogel 92, and may be branched to form a channel network inside the hydrogel. The channel network and/or a laterally-permeable tube embedded in hydrogel 92 may extend between at least a pair of channels 68a, 68b of vessel body 78. Effectors (such as differentiation factors) may be supplied via the channel network to establish concentration gradients inside the hydrogel for more controlled stem cell differentiation and organoid formation. The tubes may be created by photo-induced or thermal polymerization, among others. Pre-formed tubes also or alternatively may be incorporated into the hydrogel or scaffold for additional facilitation of liquid flow within the hydrogel/scaffold.

An open side of receptacle 82 may be sealed hermetically to produce a chamber 54 containing hydrogel 92 and scaffold 86 therein. A sealing member 80 may be bonded to the end of receptacle 82, as shown in FIG. 6. Alternatively, as described below, sealing member 80 may be created in situ by polymerization and/or solidification of a sealing fluid, at least partially inside receptacle 82. Receptacle 82 may be sealed before or after cells 96 have been placed into the receptacle, and/or before or after a medium 56 has been into receptacle 82 (and/or chamber 54) around hydrogel 92.

Figure 7:
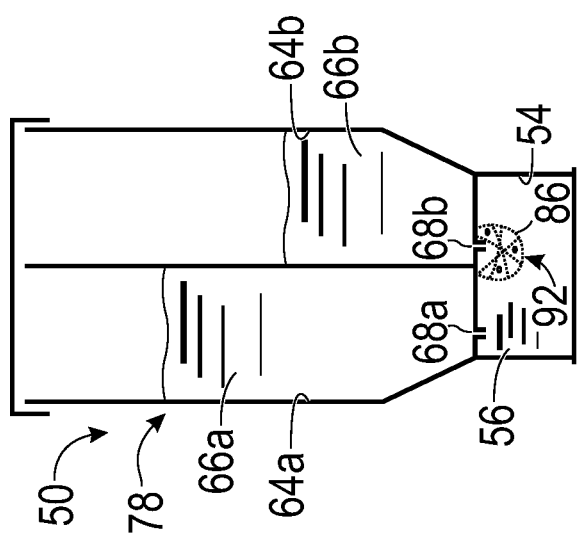
FIG. 7 is a side view of the vessel body and sealing member of FIG. 6, taken after the vessel body has been flipped over to an organoid-culturing orientation, at least one liquid medium has been introduced into the chamber containing the scaffold and into overlying reservoirs that are in fluid communication with the chamber, and a lid of the vessel has covered the open tops of the reservoirs.

Media 56, 66a, 66b may be disposed in chamber 54 and each reservoir 64a, 64b of vessel 50; see FIG. 7. The same medium may be introduced into each chamber and reservoir, or different media may be introduced, which may create a concentration gradient of one or more nutrients and/or effectors. As explained above, medium 56 may be introduced initially via an open side of receptacle 82, before the receptacle is sealed to create chamber 54. To prevent leakage of medium 56 from receptacle 82 via one or more channels 68a, 68b before chamber 54 is created, an end of each channel may be covered with hydrogel 92 (or a different hydrogel). The different hydrogel may be configured to melt below the incubation temperature (such as 37° C.) for organoid formation and culture. Alternatively, medium 56 may be introduced into chamber 54 (after the chamber is formed) from at least one reservoir 64a, 64b via at least one channel 68a, 68b.

Gravity may drive fluid into chamber 54 from one of the reservoirs, and/or between the reservoirs via the chamber if the fluid levels in the reservoirs are different. For example, in FIG. 7, the top of medium 66a in reservoir 64a is higher than the top of medium 66b in reservoir 64b. Accordingly, gravity drives flow of medium 66a into chamber 54 via channel 68a (which functions as an inlet), and out of chamber 54 via channel 68b (which functions as an outlet). Over time, the levels of media 66a, 66b will tend to equalize. Accordingly, fluid may be added to and/or removed from one or more of the reservoirs to drive further fluid flow in the same or the reverse direction, or the verticality of vessel 50 may be changed periodically (e.g., see Example 2).

Figure 9:
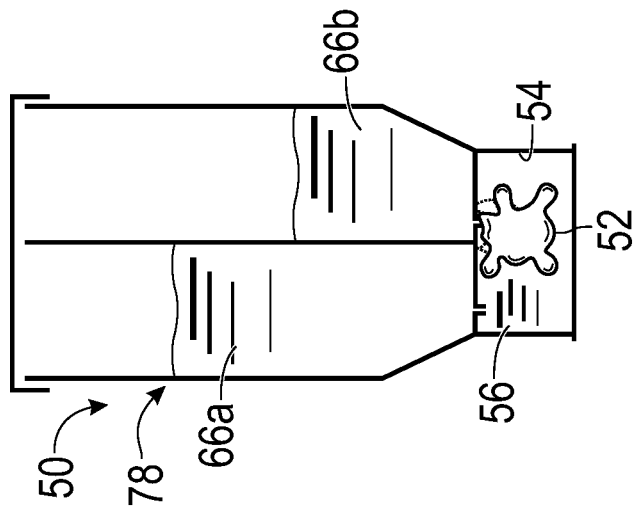
FIG. 9 is a side view of the vessel of FIG. 8 taken after remodeling/replacement of the scaffold by the developing organoid.
Figure 8:
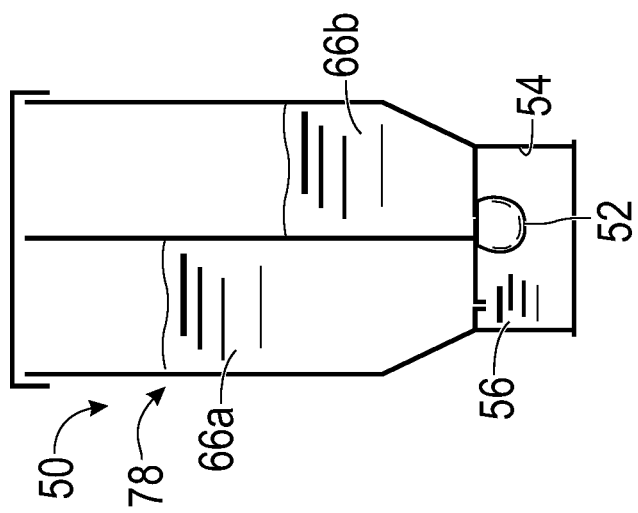
FIG. 8 is a side view of the vessel of FIG. 7 taken after proliferation and differentiation of stem cells in the scaffold to generate an organoid.

FIGS. 8 and 9 show vessel 50 containing organoid 52. The organoid is formed by proliferation and differentiation of cells 96 in hydrogel 92. In FIG. 9, the size and shape of organoid 52 have changed relative to FIG. 8, as scaffold 86 is remodeled by cells of the organoid. In other embodiments, the final size and shape of organoid 52 may be defined substantially by the size and shape of scaffold 86 when formed.

Figure 10:
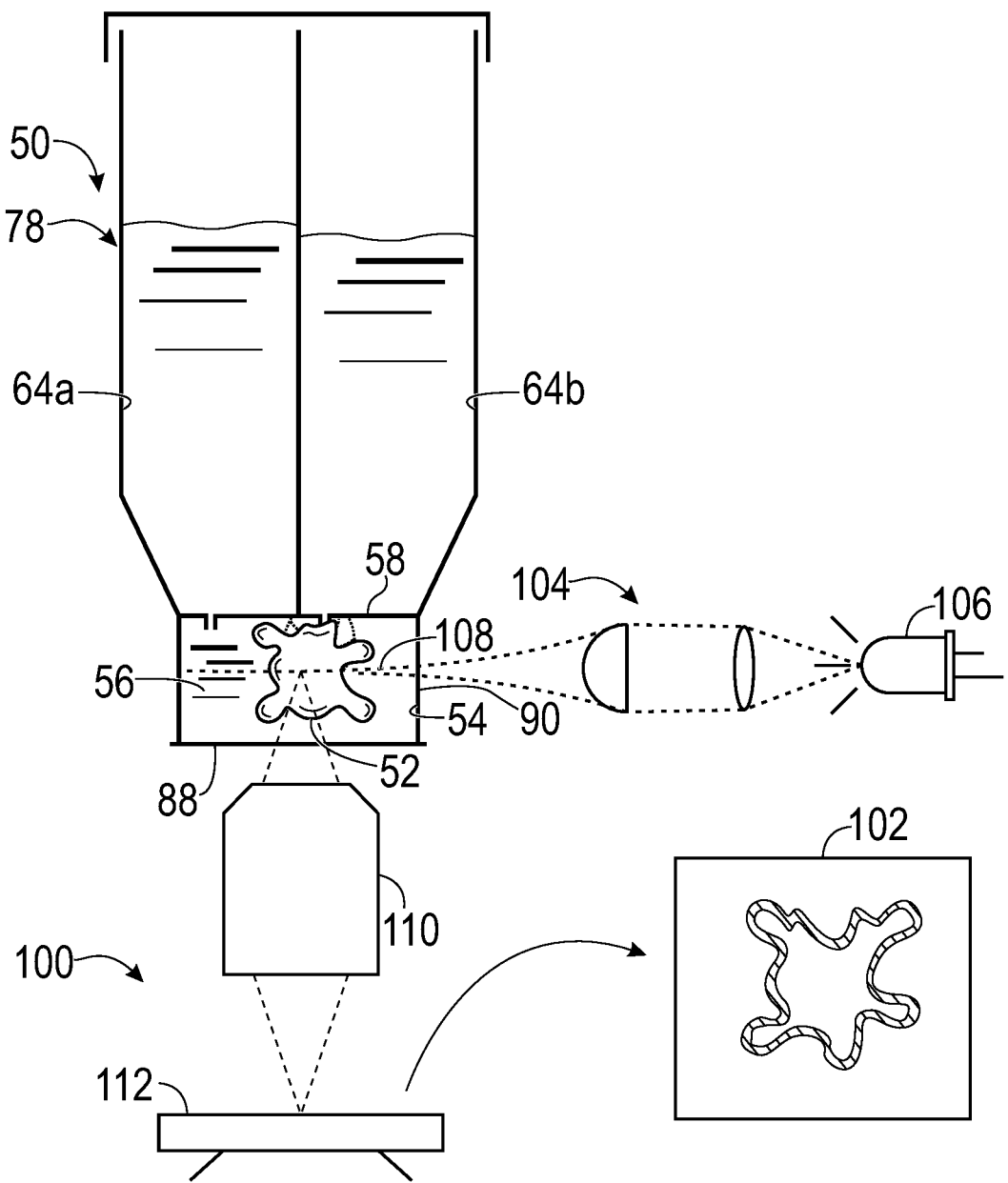
FIG. 10 is a side view of the vessel of FIG. 9 taken as the organoid is being imaged by light-sheet microscopy.

FIG. 10 shows an exemplary imaging system 100 for capturing an image 102 of organoid 52 by light-sheet microscopy. Imaging system may include an illumination assembly 104 including a light source 106 to generate light for a light sheet 108. The light sheet may be oriented horizontally, as depicted in FIG. 10, and may propagate through organoid 52 from one of lateral windows 90. Alternatively, light sheet 108 may be oriented vertically, and may propagate through organoid vertically from bottom window 88. Light may be collected from organoid 52 with an objective 110 for capture by an image sensor 112. Light that propagates through bottom window 88 may be collected, as in the depicted embodiment, or light may be collected from one of lateral windows 90. Light sheet 108 may be moved, by corresponding motion of illumination assembly 104 (or vessel 50), to permit capture of a stack of images, thereby providing three-dimensional image data for the organoid. If organoid 52 no longer needs to be viable, the organoid may be fixed and cleared before imaging, by supplying fixing and clearing reagents from one or more of reservoirs 64a, 64b through top wall 58 of chamber 54.

FIGS. 11-13 illustrate an alternative, in situ approach to sealing open side 84 of receptacle 82 to produce chamber 54. FIG. 11 shows vessel body 78 inverted, after formation of hydrogel 92 including scaffold 86. A filler hydrogel 113 also has been dispensed into open receptacle 82 via open side 84, which may prevent leakage from receptacle 82 through channel 68a. The filler hydrogel may be configured to melt or dissolve once organoid culture begins. FIG. 12 shows 3D printer 94 dispensing a sealing liquid 114 into receptacle 82. FIG. 13 shows sealing liquid 114 solidifying to hermetically seal the open side of receptacle 82 to create chamber 54.

The sealing liquid may be configured to be solidified to produce a thermoplastic polymer or a thermosetting polymer, among others. Exemplary thermoplastic polymers include a thermoplastic elastomer or wax, preferably having a melting point of less than 100° C. A lower melting point may be desirable, but at least about 50° C. The thermoplastic polymer may be dispensed in liquid form onto the surface of filler hydrogel 113, at a temperature above the melting temperature of the polymer, to form a sealing layer 116, which hardens as the layer cools to create a sealing member 80.

In other examples, the layer may be solidifiable to create a thermosetting polymer. FIG. 13 shows an example in which sealing layer 116 is solidified to a thermosetting polymer by irradiation with optical radiation (e.g., ultraviolet light) from illumination assembly 104. The illumination assembly forms a light sheet 108 that preferentially irradiates sealing layer 116 with ultraviolet light, thereby minimizing photodamage to scaffold 86 and/or cells 96 already present in receptacle 82.

FIG. 14 shows vessel body 78 flipped over to its organoid-culturing orientation, with sealing layer 116 solidified to form sealing member 80, and media 56, 66a, 66b in chamber 54 and reservoirs 64a, 64b. Objective 110 of an imaging system is collecting light from chamber 54 to form an image. Medium 56 and sealing layer 116 may have substantially the same refractive index, to improve image quality.

Figure 15:
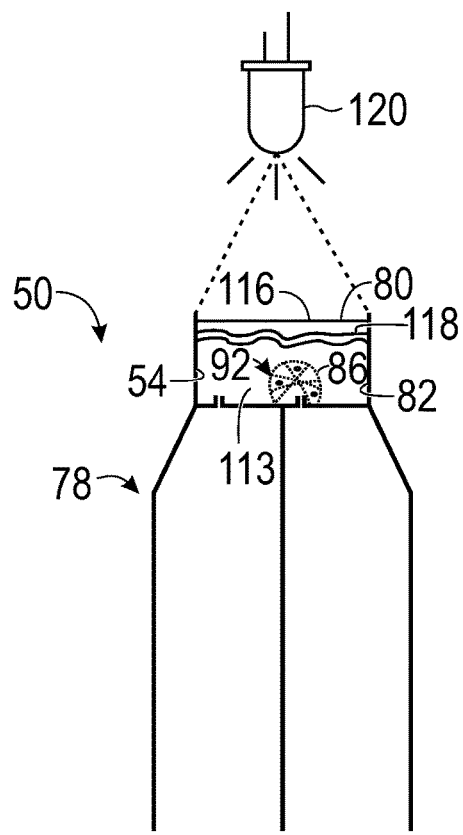
FIG. 15 is a side view of the vessel body and scaffold of FIG. 12 illustrating, relative to FIG. 13, a modified approach to sealing an open side of the receptacle of the vessel body to produce a chamber, by forming a sealing member in situ in the receptacle.

FIG. 15 illustrates a modified in situ approach for sealing an open side of receptacle 82 of vessel body 78 (compare with FIG. 13). A radiation-blocking layer 118 may be formed on the surface of filler hydrogel 113, before layer 116 of a thermosetting sealing liquid is added to receptacle 82. Layer 116 may be irradiated with optical radiation from a light source 120 positioned above vessel body 78, to encourage solidification of layer 116 to form a sealing member 80. Radiation-blocking layer 118 shields hydrogel 92 from photodamage.

III. EXAMPLES

This section describes further embodiments of systems and methods for organoid formation, culture, monitoring, and/or analysis. These embodiments are intended for illustration only and should not limit the entire scope of the present disclosure.

Example 1

Strip for Organoid Cultures

Figure 16:
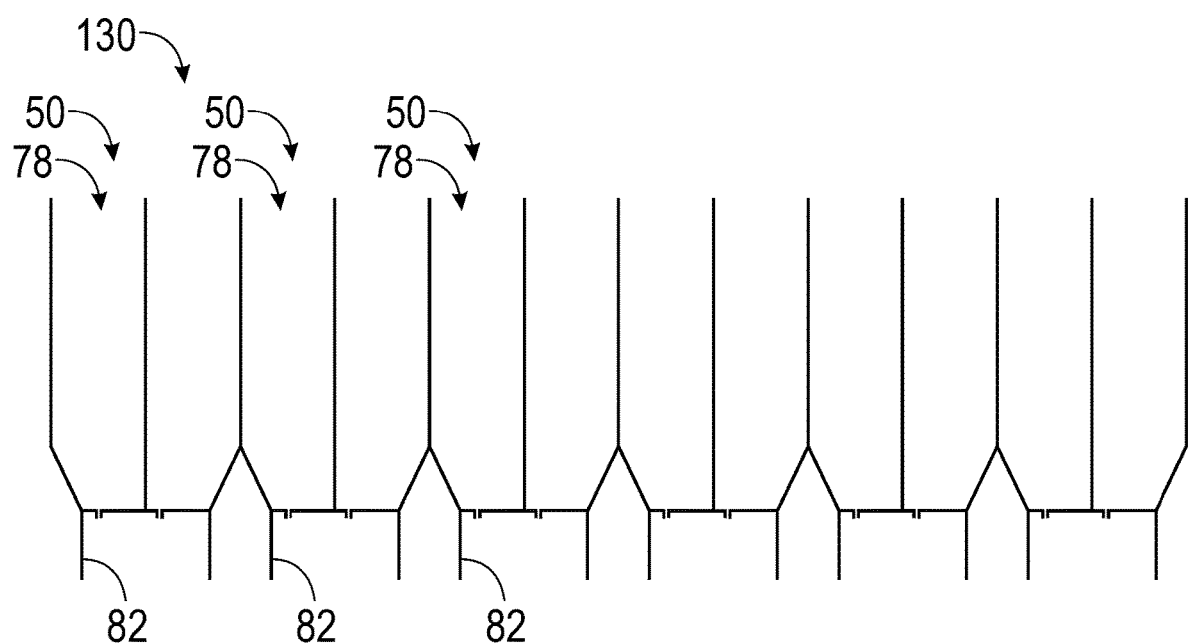
FIG. 16 is a schematic side view of an exemplary vessel strip for forming, culturing, monitoring, and/or analyzing an array of organoids, where the vessel strip has a set of vessels connected directly to one another.

This example describes an exemplary strip 130 for forming, culturing, monitoring, and/or analyzing an array of organoids; see FIG. 16.

Strip 130 may include an array of vessel bodies 78 connected to one another. The vessel bodies may be formed integrally with one another, or formed separately and then connected to one another after formation (and/or after receptacles 82 are sealed to form chambers 54 (also see FIG. 1). Separately-formed vessel bodies 78 may be connected to one another by bonding, an interference fit, fasteners, or a holder (e.g., see Example 6), among others. The vessel bodies may be connected to one another to create a linear or at least two-dimensional array of receptacles 82.

Example 2

Fluid Transfer Between Vessel Reservoirs

This example describes exemplary configurations to transfer fluid between reservoirs 64*a*, 64*b* of the same or different vessels 50; see FIGS. 17, 17A, 17B, and 18.

Figure 17:
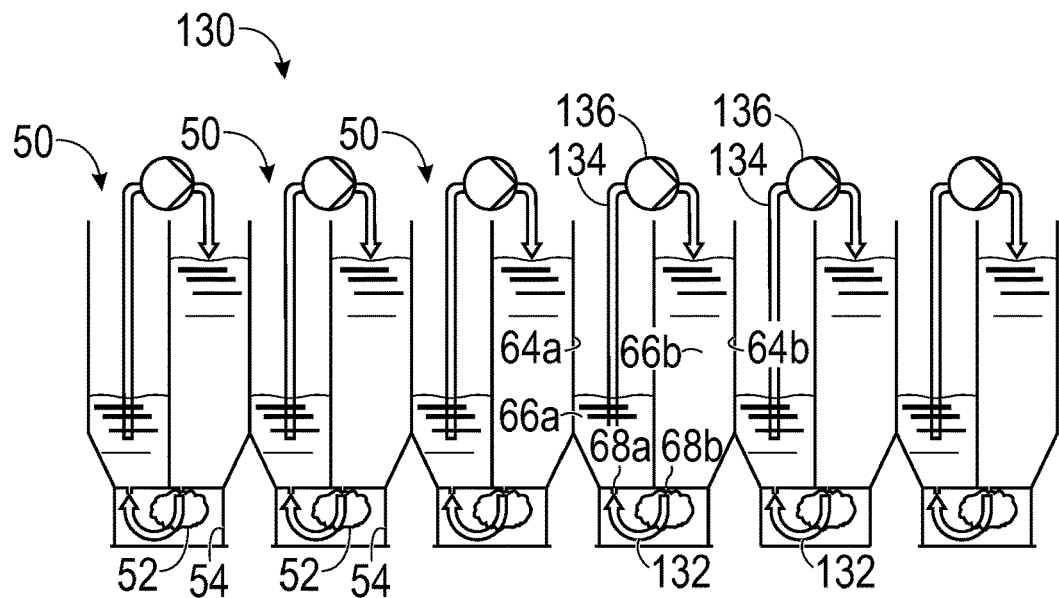
FIG. 17 is a schematic side view of the vessel strip of FIG. 16, taken during culture of organoids and illustrating an exemplary pump configuration to transfer a liquid medium between reservoirs within each vessel of the vessel strip.

FIG. 17 shows strip 130 during culture of organoids 52 in chambers 54. Each vessel 50 has a separate flow cycle indicated by arrows 132, 134. Flow 132 through each chamber 54, between channels 68*b* and 68*a*, is driven by gravity as a result of the difference in levels of media 66*a*, 66*b* in respective reservoirs 64*a*, 64*b*. Replenishing flow 134 from reservoir 64*a* to reservoir 64*b* is driven by a pump 136. The flow rate of pump 136 can be adjusted to keep the respective levels of media 66*a*, 66*b* substantially constant, such that fluid passes through chamber 54 at a substantially constant rate. This flow may apply pressure on organoid 52, which can promote its growth and development. In other examples, the flow rate of pump 136 can be varied, to apply a varying pressure on organoid 52.

Figure 17A:
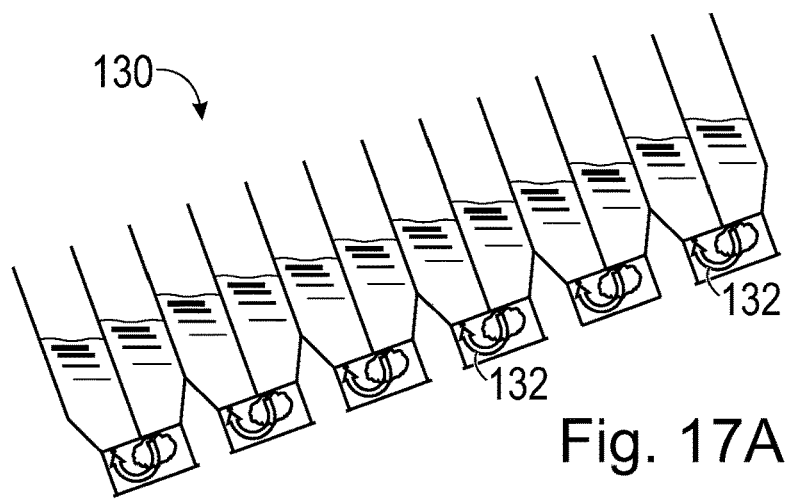
FIGS. 17A and 17B show schematic side views of the vessel strip of FIG. 16, taken during culture of organoids and illustrating how tilting the vessel strip in opposite rotational directions can drive flow in respective opposite directions within each chamber.
Figure 17B:
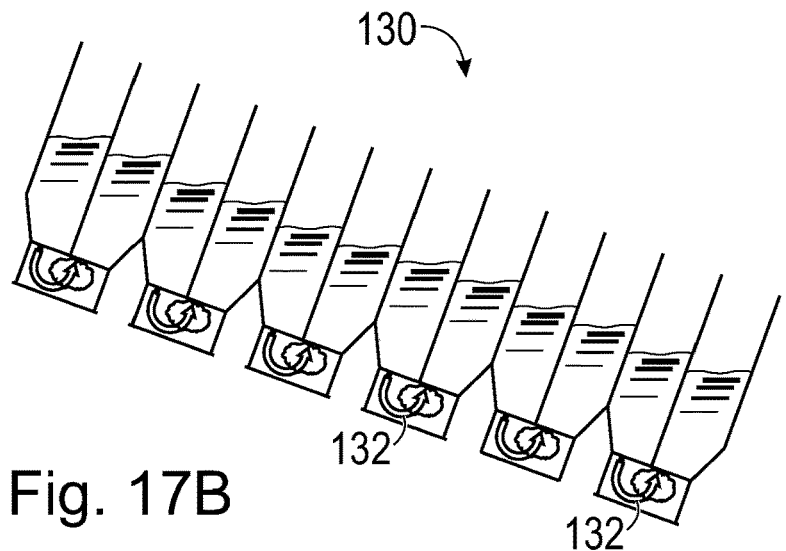

In other embodiments, pump 136 can be eliminated, as shown for vessel strip 130 in FIGS. 17A and 17B. Strip 130 may be rocked to tilt the holder from vertical at a suitable rate, in order to periodically reverse the direction of gravity-driven flow 132. In other words, the holder may be tilted in one direction to drive fluid from reservoir 64*a* to 64*b* within each vessel 50, and then tilted in the opposite rotational direction to drive fluid from reservoir 64*b* to 64*a* within each vessel 50, via channels 68*a*, 68*b*.

Figure 18:
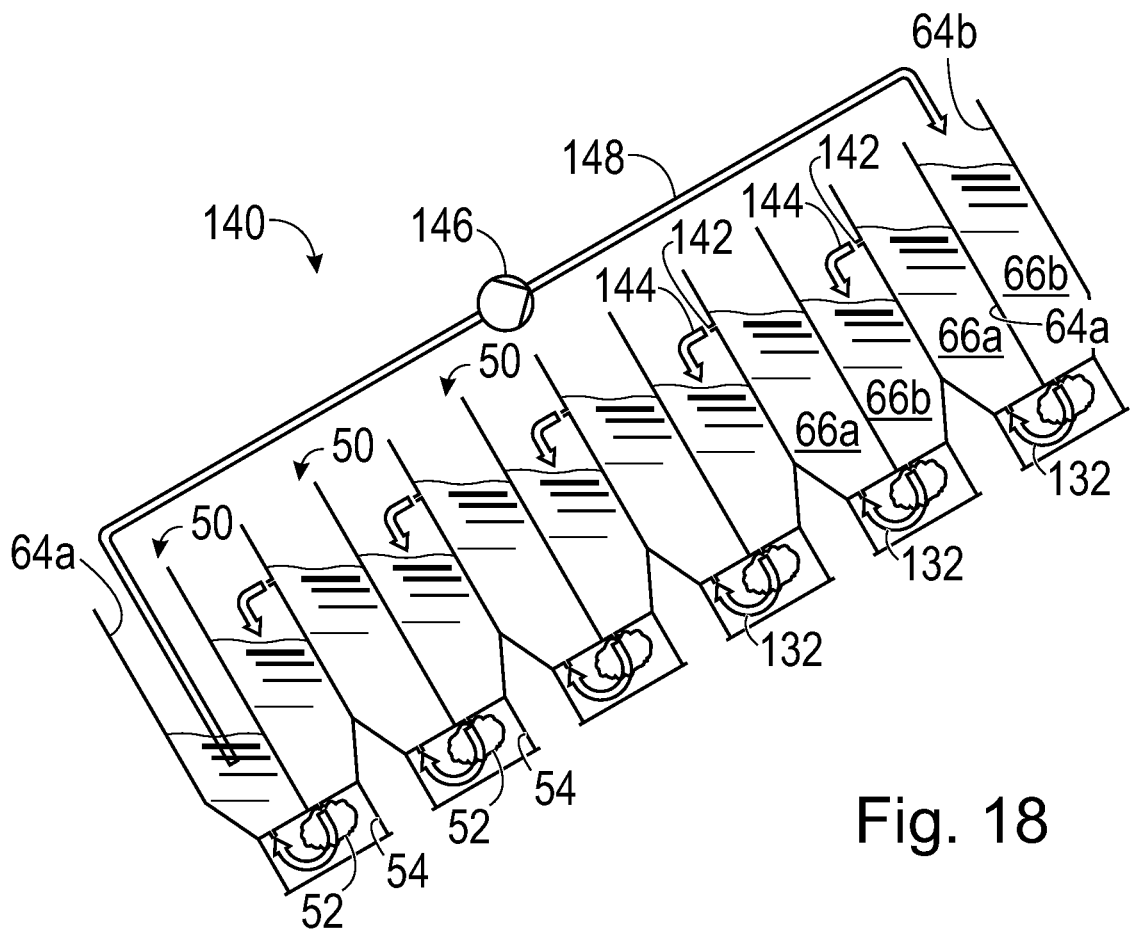
FIG. 18 is a schematic side view of another embodiment of an exemplary vessel strip having an array of vessels, taken during culture of organoids and illustrating an exemplary pump configuration to transfer a liquid medium among reservoirs of different vessels of the vessel strip.
Figure 19:
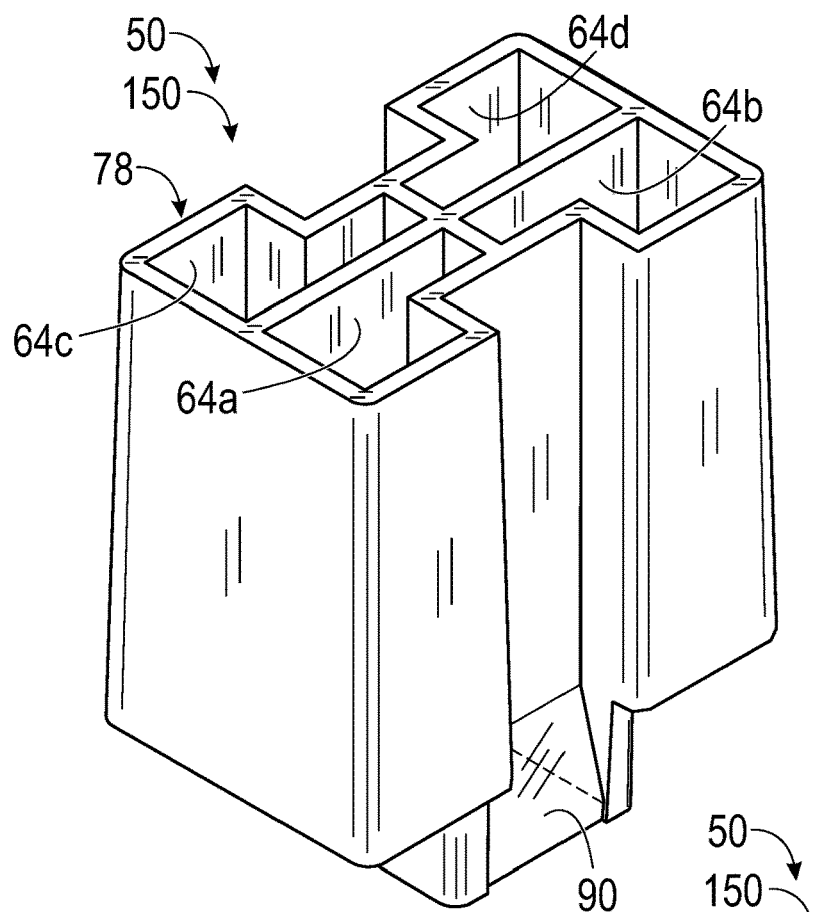
FIG. 19 is a view of an exemplary embodiment of a vessel body for the vessel of FIG. 2.
Figure 20:
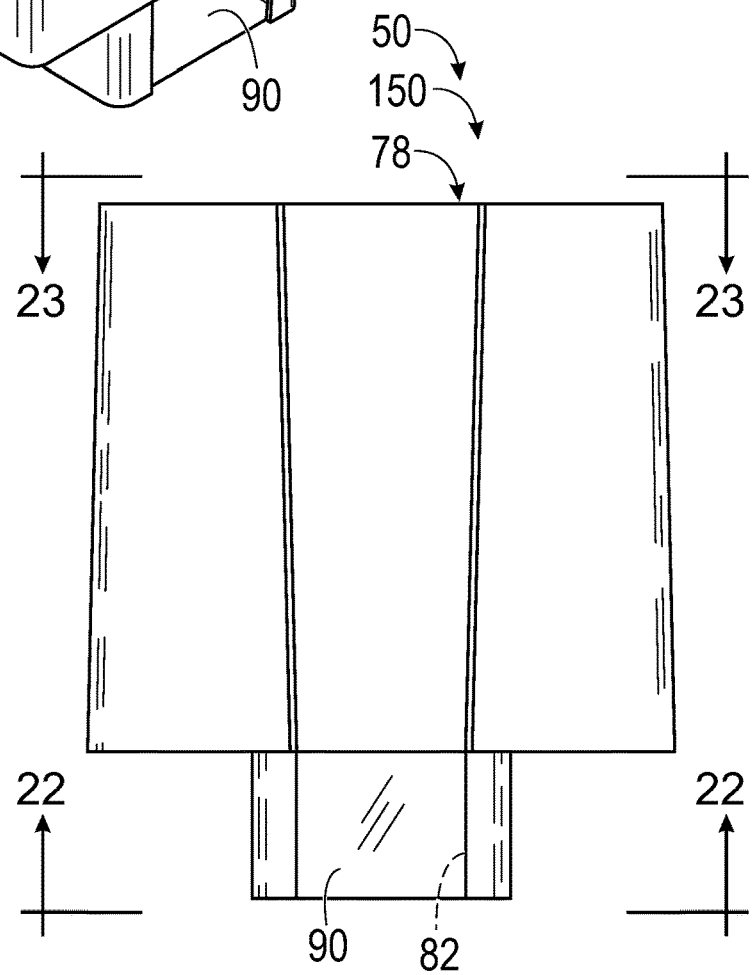
FIG. 20 is a front view of the vessel body of FIG. 19.
Figure 21:
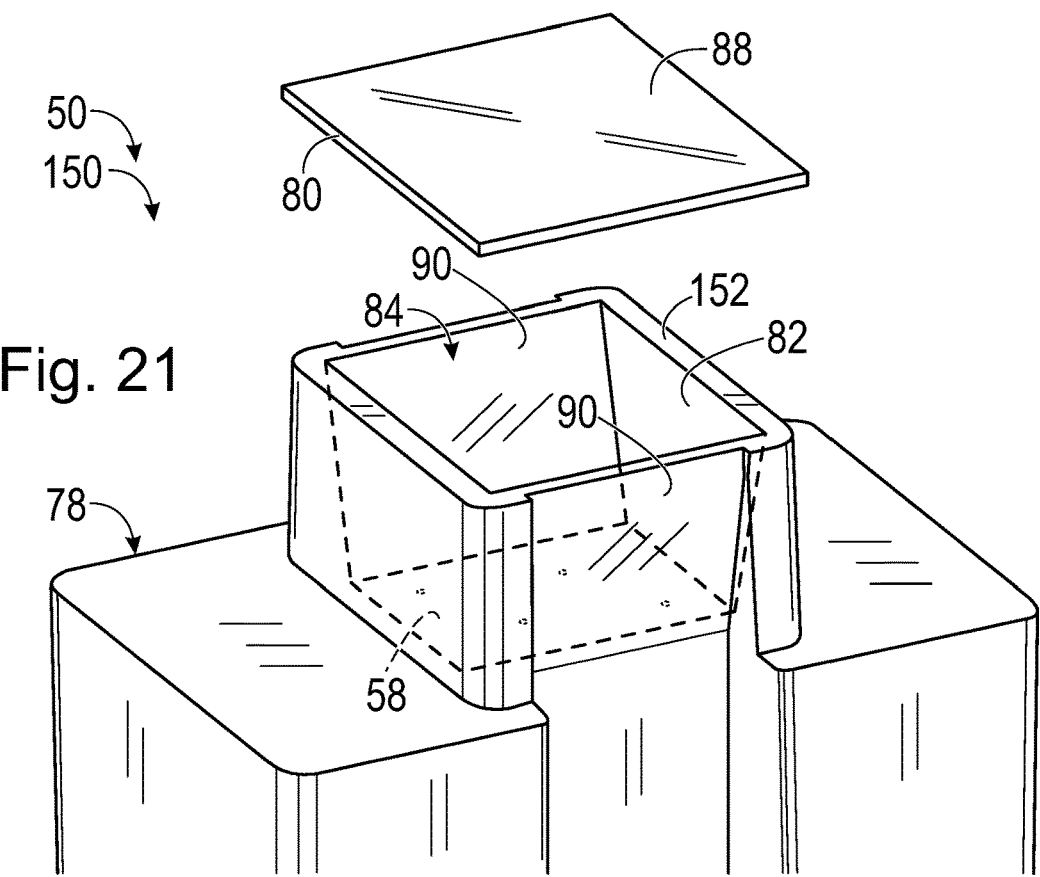
FIG. 21 is a view of the vessel body of FIG. 19, taken with the vessel body inverted and with a pre-made sealing member exploded from a receptacle of the vessel body.
Figure 22:
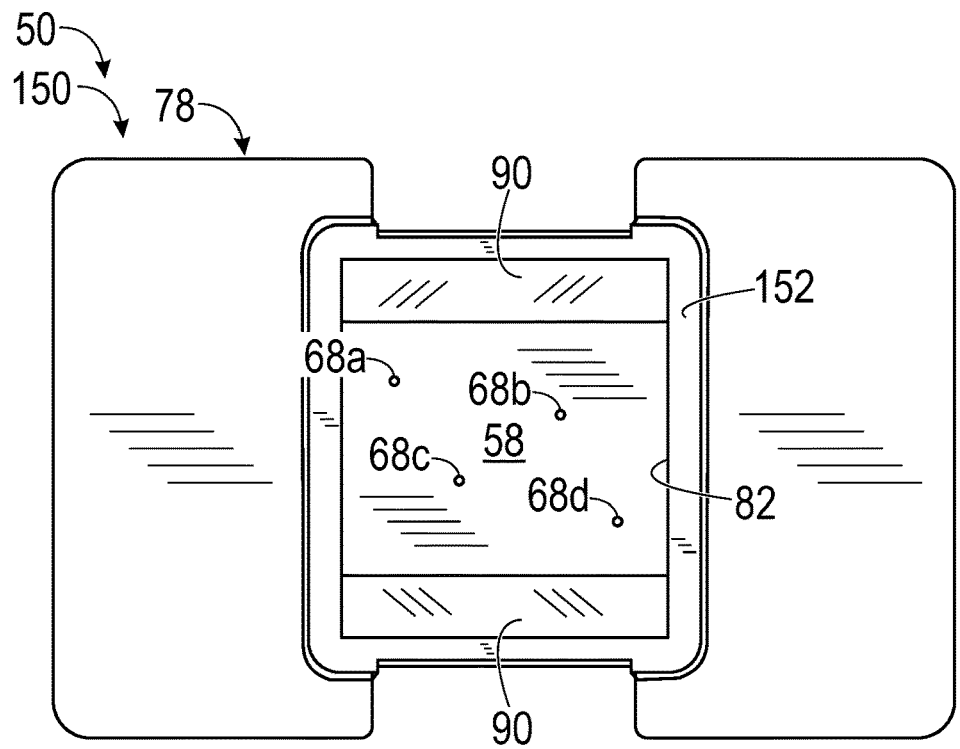
FIG. 22 is a bottom view of the vessel body of FIG. 19, taken generally along line 22-22 of FIG. 20.

FIG. 18 shows another strip 140 during culture of organoids 52 in chambers 54. Strip 140 is similar to strip 130 of FIGS. 16 and 17, with flow 132 driven between channels 68*a*, 68*b* of each vessel 50. However, a respective channel 142 provides fluid communication between each adjacent pair of vessels 50. More specifically, each channel 142 allows fluid to flow directly from reservoir 64*a* of one vessel 50 to reservoir 64*b* of an adjacent vessel 50, as indicated by flow arrow 144, or vice versa. To maintain fluid circulation, strip 140 can be periodically tilted (as in FIG. 18) to drive fluid from left to right, toward one end of the holder, and then tilted in the opposite rotational direction, to drive fluid from right to left toward the opposite end of the holder. A pump 146 may transfer media between reservoirs 64*a*, 64*b* located at opposite ends of strip 140, indicated by a flow arrow at 148. The pump can be used instead of, or in addition to, periodically tilting strip 140.

Example 3

Vessel Embodiment

This example describes an exemplary embodiment 150 of vessel 50 of Section I having a vessel body 78 formed by injection molding and defining four reservoirs 64*a*-64*d*; see FIGS. 19-25.

Figure 23:
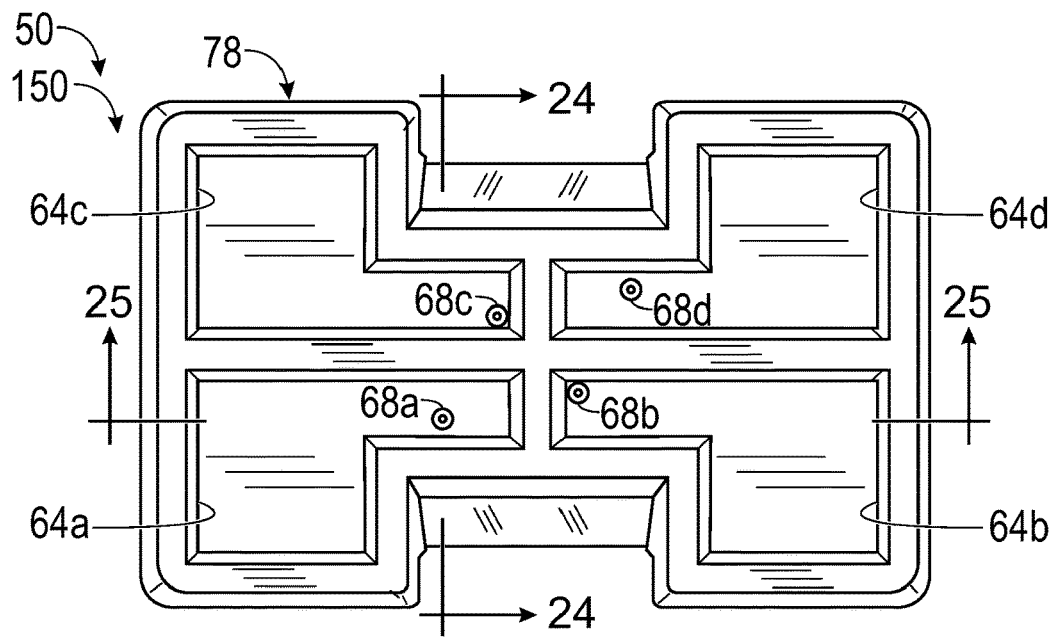
FIG. 23 is a top view of the vessel body of FIG. 19, taken generally along line 23-23 of FIG. 20.
Figure 24:
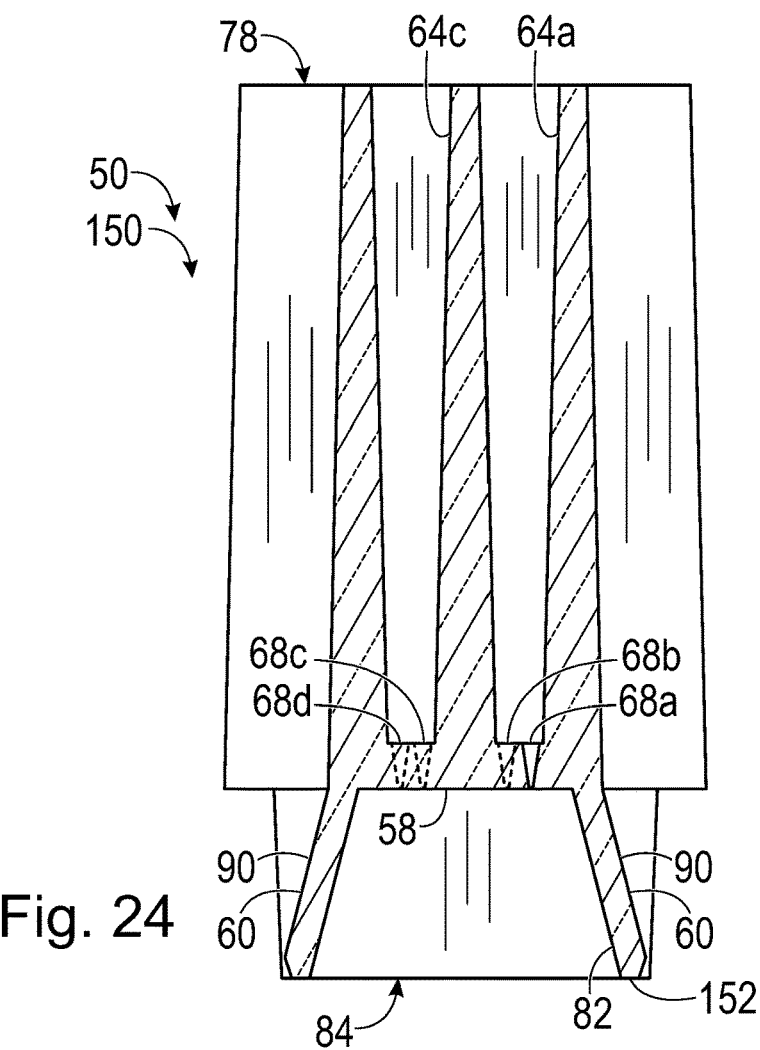
FIG. 24 is a sectional view of the vessel body of FIG. 19, taken generally along line 24-24 of FIG. 23.
Figure 25:
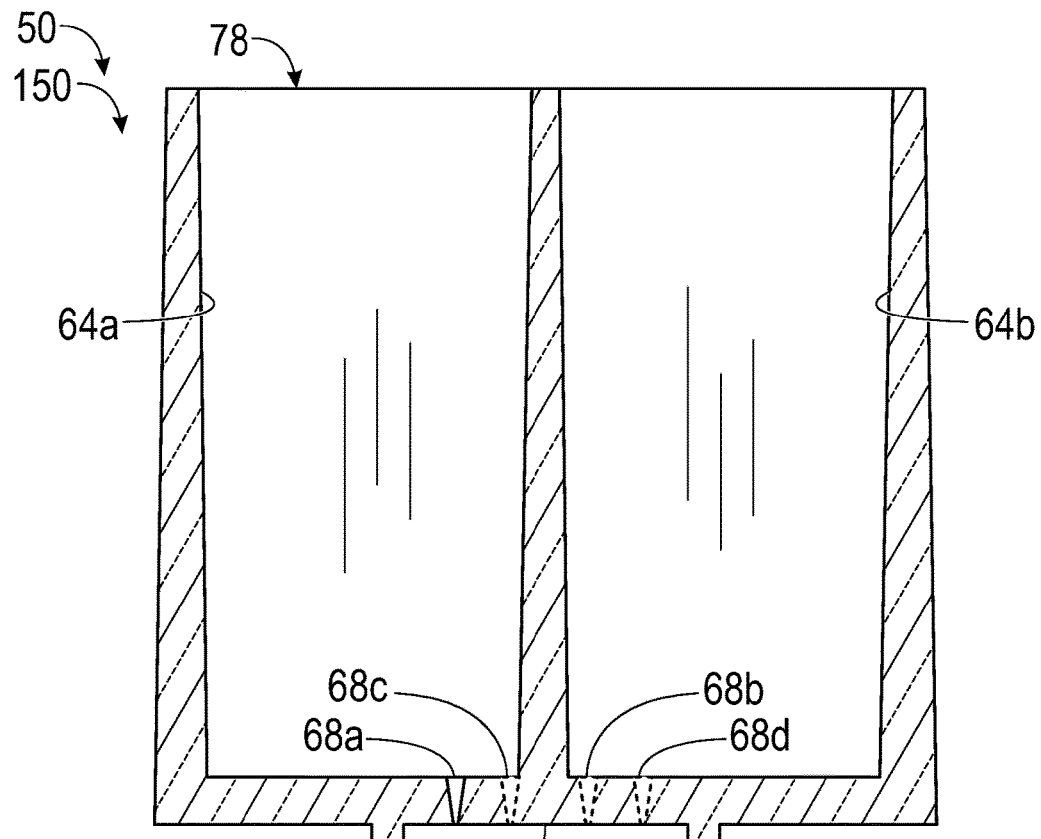
FIG. 25 is another sectional view of the vessel body of FIG. 19, taken generally along line 25-25 of FIG. 23.

Each reservoir 64*a*-64*d* may be in fluid communication with receptacle 82 (and/or chamber 54) via a corresponding channel 68*a*-68*d* extending through top wall 58 of receptacle 82 (and/or chamber 54) (see FIGS. 23 and 25). The upper end of each channel may be flush with top wall 58 (see FIG. 25).

Various optical windows may be incorporated into vessel 150. A planar sealing member 80 (e.g., similar to a microscope cover slip) may provide a bottom window 88 of chamber 54, after the sealing member has been bonded to a bottom end surface 152 of vessel body 78 (see FIG. 21). The vessel body may include a pair of lateral windows 90 (see FIGS. 19-21), which may be slanted somewhat from vertical to facilitate manufacture by injection molding (see FIG. 24).

Example 4

Vessels with Tubes

Figures 26, 27:
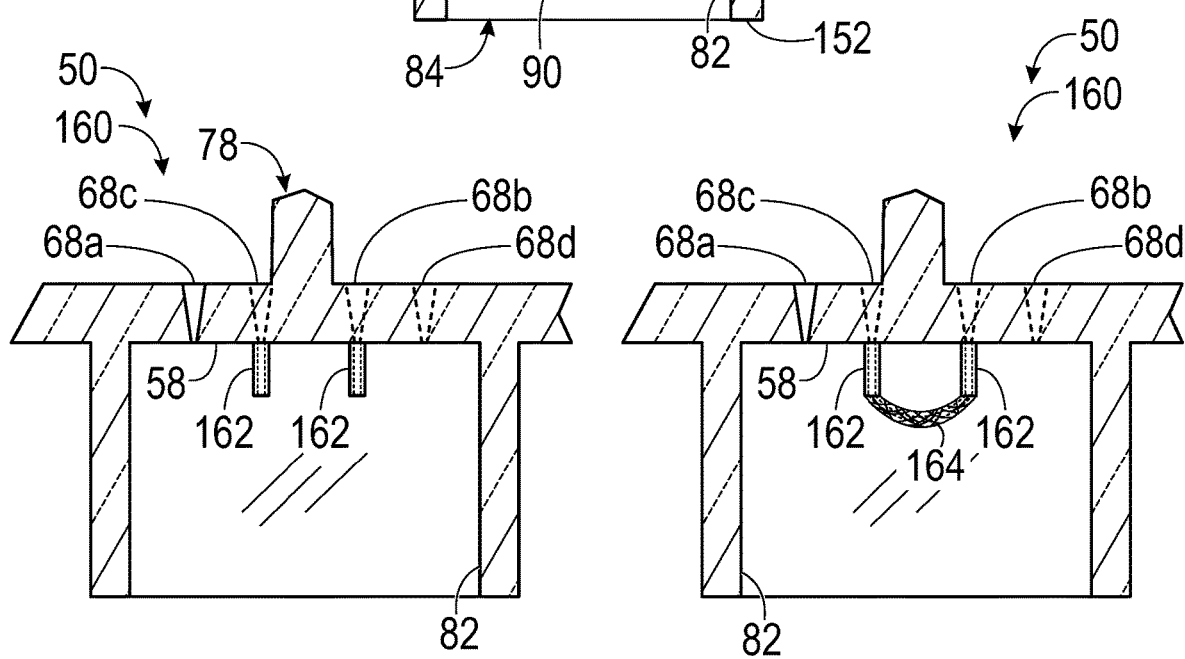
FIG. 26 is a fragmentary sectional view of another embodiment of a vessel body, taken generally as in FIG. 25, except showing only a lower portion of the vessel body that differs from that of FIG. 25.
FIG. 27 is a fragmentary sectional view of the vessel body of FIG. 26 taken after a porous tube has been formed by 3D printing between channels of the vessel body.

This example describes exemplary vessels having tubes that are pre-formed and/or formed in situ; see FIGS. 26 and 27.

FIG. 26 shows another embodiment 160 of vessel 50, for comparison with vessel 150 in FIG. 25. Channels 68*a*-68*d* of vessel 160 differ from those of vessel 150. More particularly, channels 68*b* and 68*c* are defined in part by annular protrusions 162 projecting from a bottom side of top wall 58 of receptacle 82 (and/or chamber 54). The lumens of any or all of the channels may be formed at least in part by an annular protrusion.

FIG. 27 shows a laterally porous, tubular extension 164 that may be formed in situ on one or more annular protrusions 162 by 3D printing. Each tubular extension may or may not be branched. In the depicted embodiment, tubular extension 164 connects channels 68*b* and 68*c* to one another. In other embodiments, a porous, tubular network may be formed, which may connect any suitable subset or all of the channels to one another. Each tubular extension 164 may be supported by, and/or embedded in hydrogel 92 (see Section II). The tubular extension may have the same composition as the hydrogel or may have a different composition, to, for example, minimize/promote cell attachment and/or remodeling, among others.

Example 5

Vessel with Electromagnet

Figure 28:
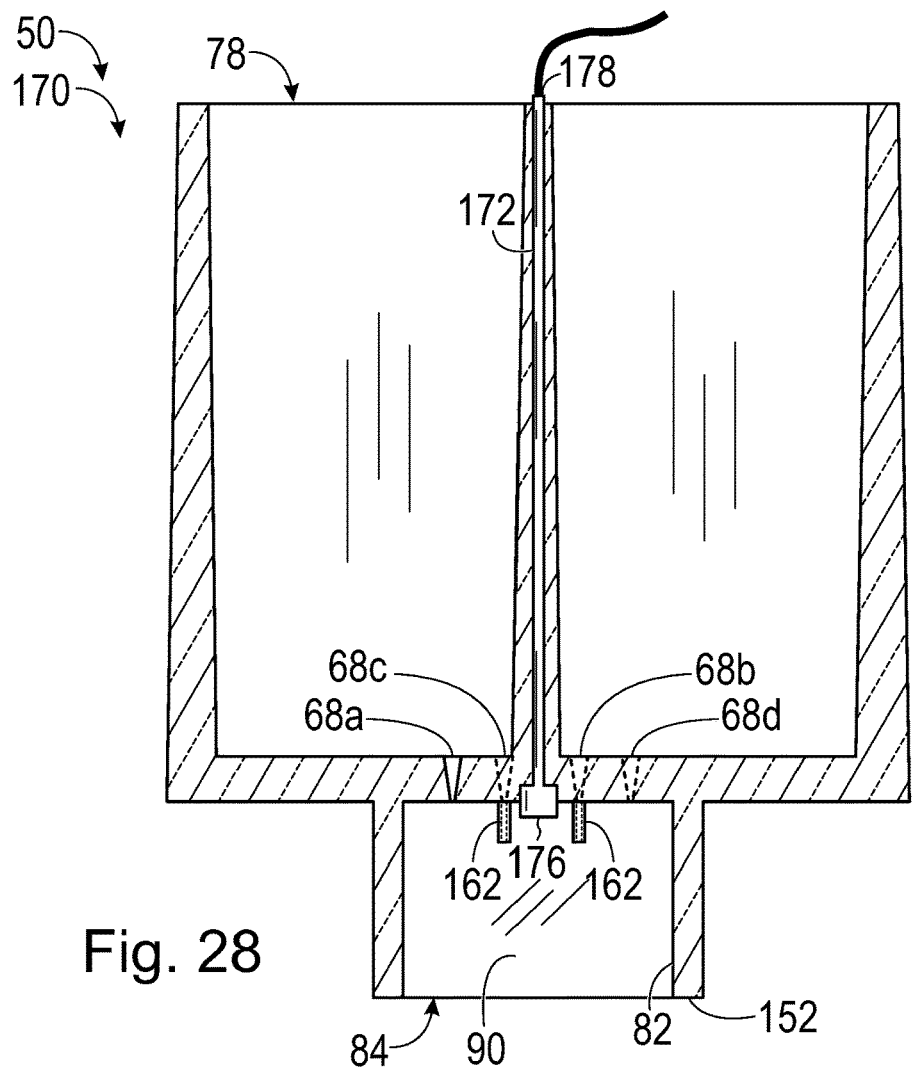
FIG. 28 is a sectional view of yet another embodiment of a vessel body, taken as in FIG. 25, with the vessel body including an electromagnet operatively associated with the receptacle of the vessel body.
Figures 29, 30:
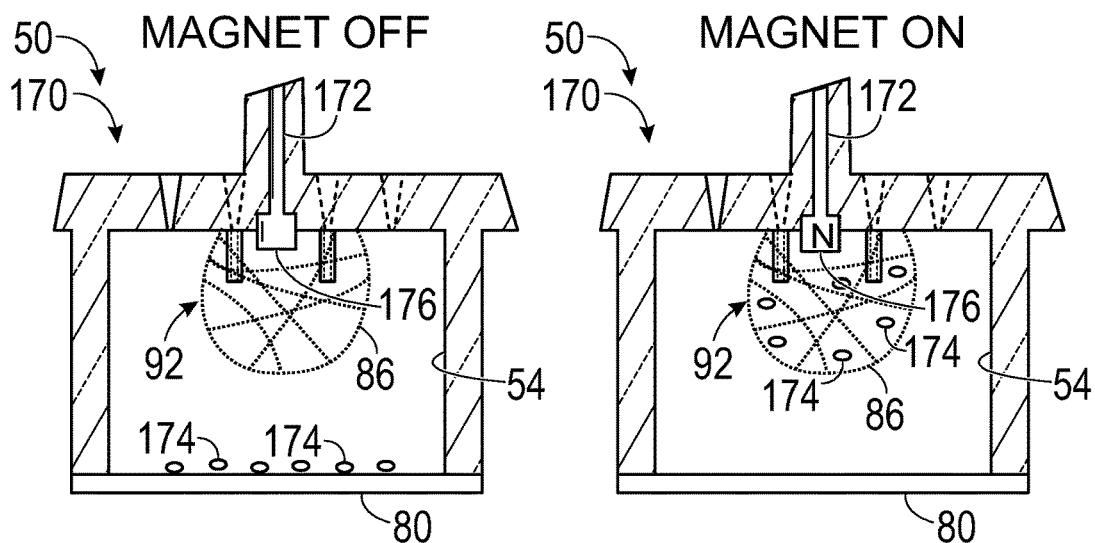
FIG. 29 is a fragmentary view of the vessel body of FIG. 28 bonded to a sealing member to create a chamber, with a scaffold connected to a ceiling of the chamber, and with cells located on a floor of the chamber, the cells being ferromagnetic, and the electromagnet turned off.
FIG. 30 is another fragmentary view of the vessel body, sealing member, scaffold, and cells of FIG. 29, taken with the electromagnet turned on such that the ferromagnetically-labeled cells have been pulled into the scaffold by magnetic force.
Figure 31:
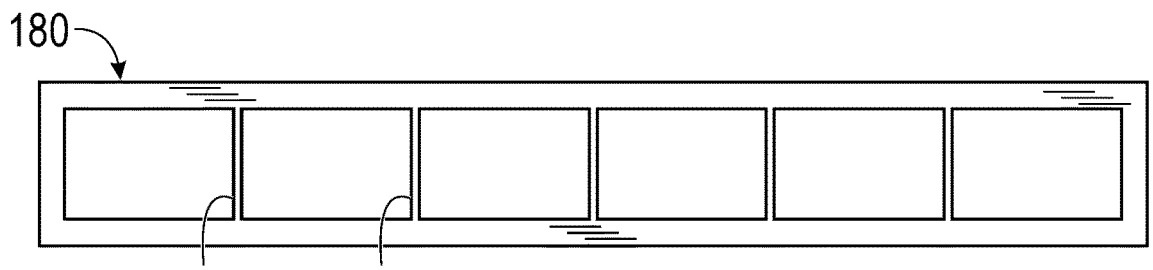
FIG. 31 is a top view of an exemplary rack to hold a linearly-arranged set of vessels as a strip during scaffold creation and organoid formation and culture, where each vessel includes a vessel body corresponding to the embodiment of FIG. 19.
Figure 32:
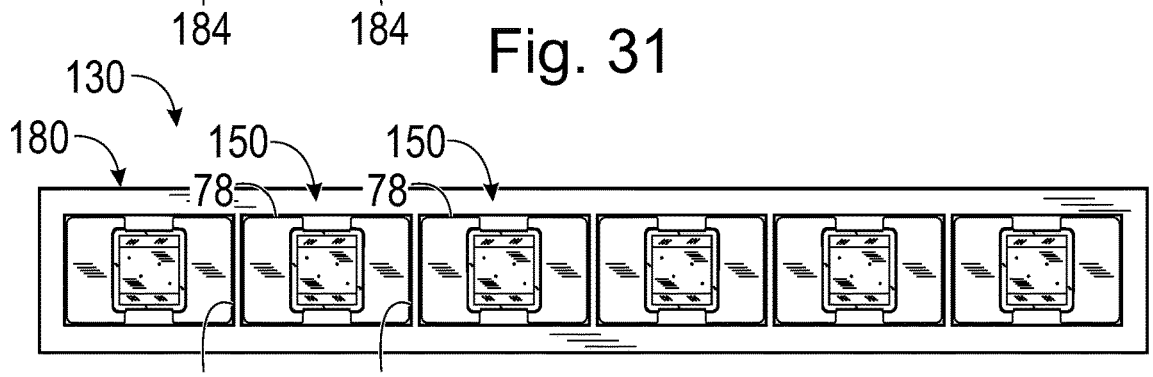
FIG. 32 is a top view of the rack of FIG. 31 assembled with a set of vessel bodies corresponding to the embodiment of FIG. 19 to create a strip.
Figure 33:
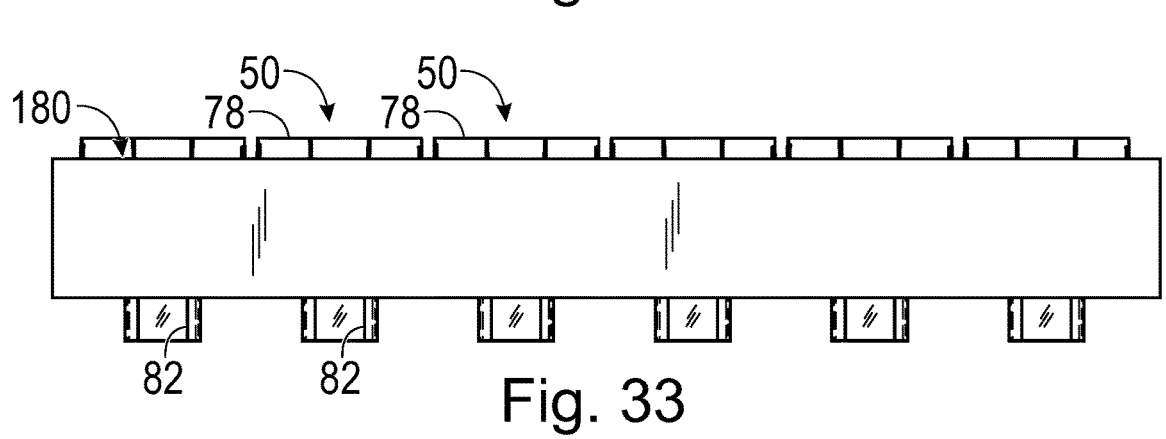
FIG. 33 is a side view of the strip of FIG. 32.
Figure 34:
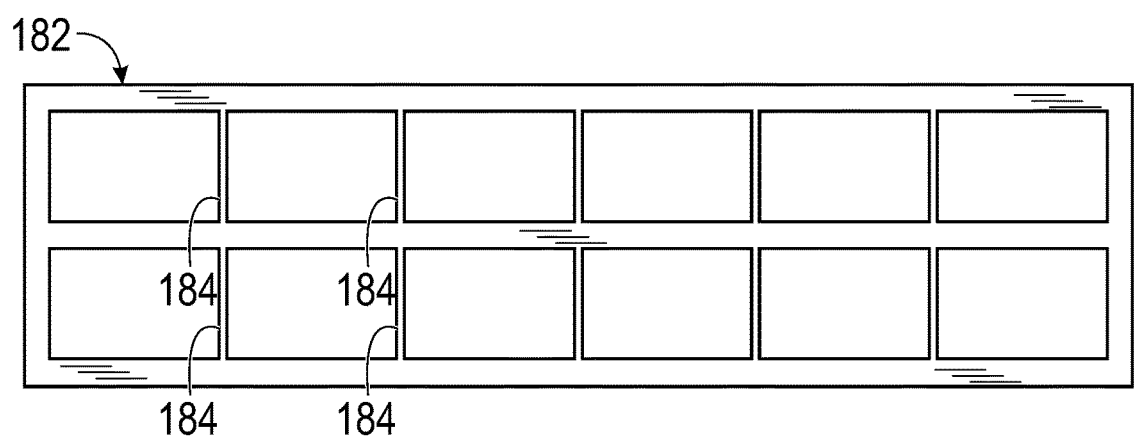
FIG. 34 is a top view of another exemplary rack to hold a two-dimensional array of vessel bodies corresponding to the embodiment of FIG. 19 to create a strip.

This example describes an exemplary embodiment 170 of vessel 50 having an electromagnet 172 positioned to attract ferromagnetically-labeled cells 174 when the electromagnet is energized (i.e., turned on); see FIGS. 28-30.

Vessel 170 may be constructed similarly to vessel 150 and may have any suitable combination of vessel features disclosed herein (see FIG. 28). Electromagnet 172 may have a working end 176 located very near or in receptacle 82 and/or chamber 54, close to at least one of channels 64*a*-64*d*. In the depicted embodiment, working end 176 is centered between channels 64*b* and 64*c*. The electromagnet may be energized via an upper end 178 thereof.

FIGS. 29 and 30 illustrate how electromagnet 172 may be utilized to attract ferromagnetically-labeled cells 174 to hydrogel 92 and/or scaffold 86 inside chamber 54. Scaffold 86 and hydrogel 92 may be formed as described above. Ferromagnetically-labeled cells 174 may be introduced into receptacle with medium 56, before the receptacle is sealed to form chamber 54, or after sealing, from one or more overlying reservoirs via one or more channels 68*a*-68*d*. In any event, ferromagnetically-labeled cells 174 are initially outside of hydrogel 92, and may settle to the bottom chamber 54, as in FIG. 29, before the electromagnet is turned on. FIG. 30 shows how energizing the electromagnet attracts ferromagnetically-labeled cells 174 to and/or into scaffold 86. Ferromagnetically-labeled cells may be associated with a ferromagnetic material (e.g., compounds containing iron, cobalt, and/or nickel, among others) before the cells are introduced into the receptacle/chamber. For example, cells may be fed ferromagnetic particles (such as iron oxide particles) to render the cells ferromagnetic or may be coated with a ferromagnetic probe, among others.

Example 6

Rack for Vessel Modules

This example describes exemplary racks 180, 182 to hold vessels 150, respectively in a linear array or two-dimensional array to form a strip 130; see FIGS. 31-34.

Each rack 180, 182 (interchangeably called a holder) has a series of openings 184 to receive vessel bodies 78 of vessels 150. Openings 184 may be arranged along the same line (rack 180) or in a rectangular grid pattern (rack 182), among others. Each vessel body 78 may be removably placed into opening 184. The opening may be sized and shaped to prevent the vessel body from passing completely through the opening. The vessel body may be coupled to opening 184 by any suitable mechanism, including a snap-fit or a separate retainer, among others.

Example 7

Vessels with Access Tubes

This example describes exemplary vessels that include access tubes, and use of the access tubes to receive various instruments; see FIGS. 35-51.

Figure 35:
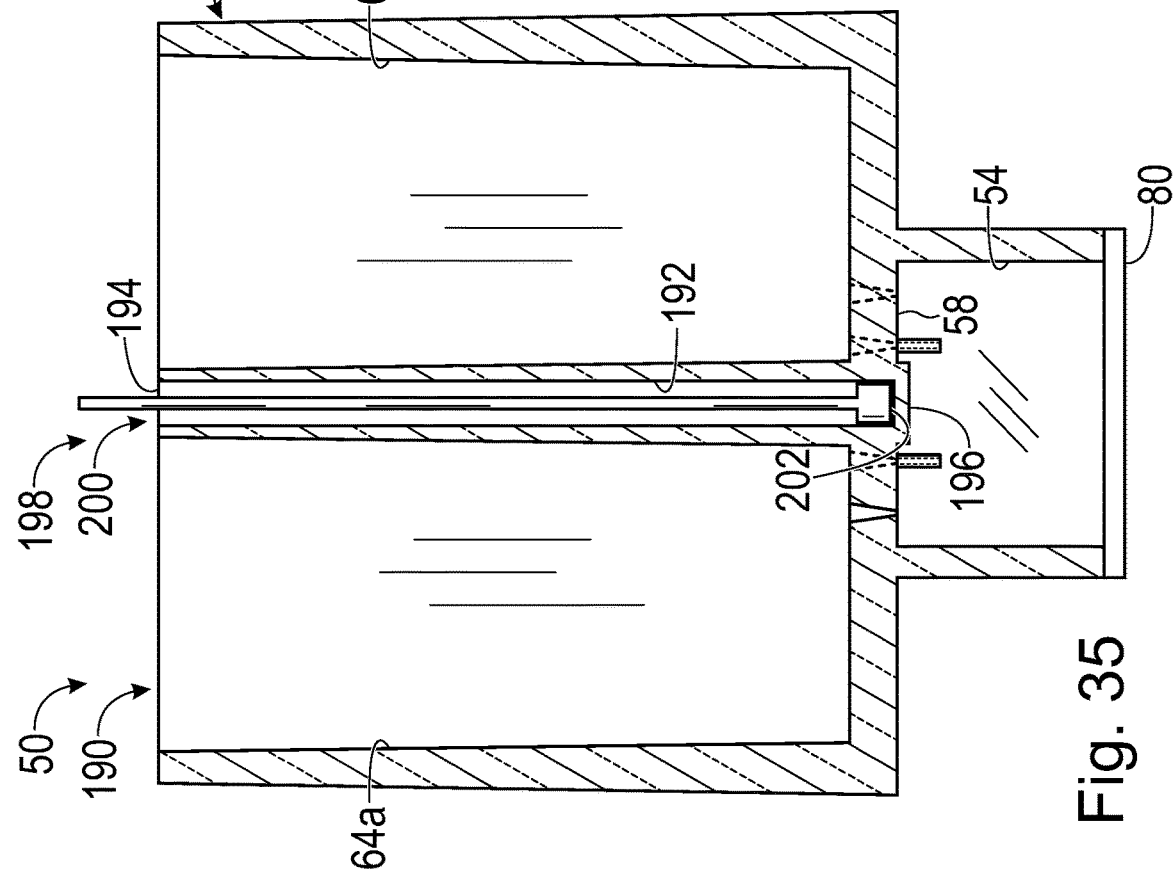
FIG. 35 is a sectional view of still yet another embodiment of a vessel body for the vessel of FIGS. 1 and 2, taken generally as in FIG. 25 (for a related embodiment), with an open bottom end of the vessel body sealed with a sealing member to form a chamber, with the vessel body defining an access tube that is closed at its bottom end by a breachable barrier, and with a magnet inserted into the access tube to place a working end of the magnet adjacent (and above) the breachable barrier.

FIG. 35 shows an embodiment 190 of vessel 50 including vessel body 78 sealed at its bottom end with a sealing member 80 to form a chamber 54. Vessel body 78 is similar to that described above for vessel 160 (see FIG. 26), except that the vessel body defines at least one access tube 192. The access tube is open at its top end 194, but may have a bottom end that is closed by a barrier 196. The barrier may be a wall region of top wall 58 of the chamber that is shared between access tube 192 and chamber 54, and that prevents fluid communication between the access tube and the chamber, while the barrier is intact. Chamber 54 and reservoirs 64a, 64b are not shown as containing fluid (e.g., medium or other liquid) in any of the figures of Example 7 to simplify the drawings.

Barrier 196 may be configured to be breached by a sharp or blunt instrument, as described further below, to access chamber 54. Accordingly, the barrier may be thinner than adjacent regions of top wall 58, as shown in FIG. 35, and/or may include predefined structure (e.g., predefined frangible regions of lesser thickness) at which the barrier can be preferentially torn or otherwise breached with a suitable instrument.

FIG. 35 shows an exemplary instrument 198 inserted into access tube 192. Here, instrument 198 is a permanent magnet 200, with a pole 202 of the magnet adjacent barrier 196. In other embodiments, the magnet can be an electromagnet or any of the other instruments disclosed herein. Magnet 200 may be sufficiently strong to form a magnetic field that extends into chamber 54 while barrier 196 is intact. In other cases, the bottom end of magnet 200 may be inserted into chamber 54 after barrier 196 is breached (and even may breach the barrier). Whether or not the magnet enters chamber 54, the magnet can apply attractive force to ferromagnetic items (e.g., ferromagnetically-labeled cells) inside chamber 54. The magnet may be retractable/removable and/or may be firmly attached to access tube 192.

Figure 36:
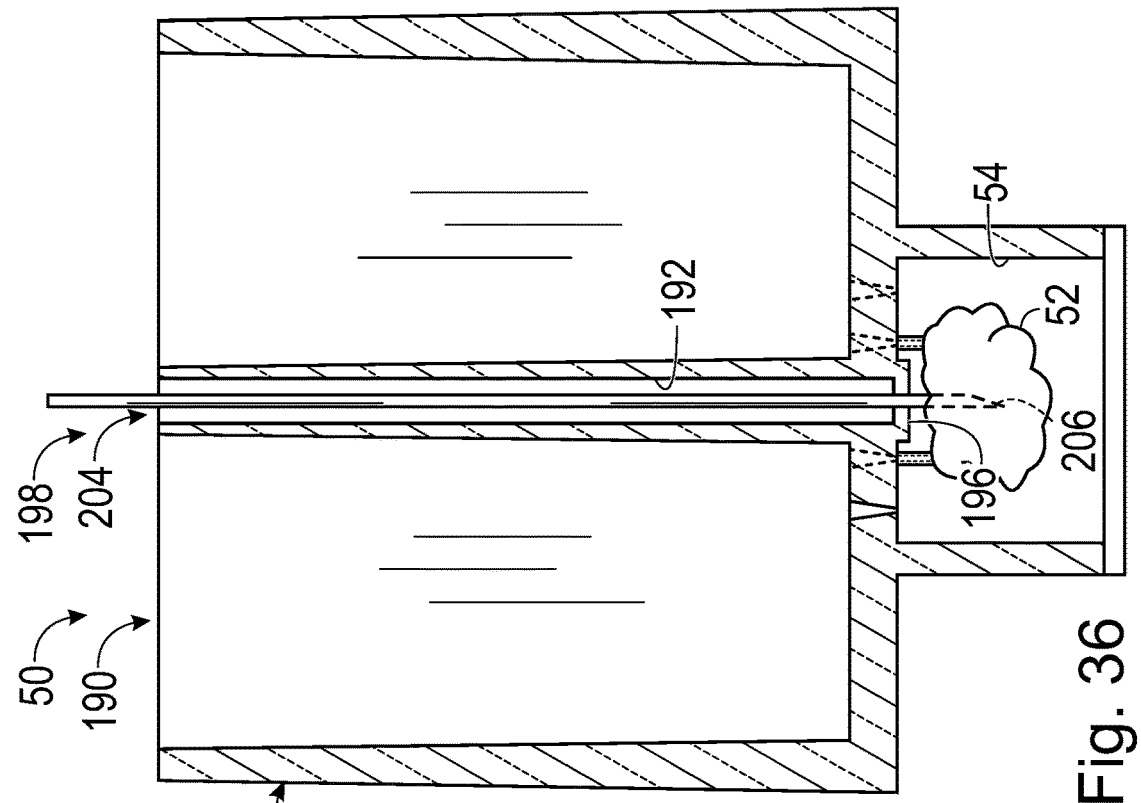
FIG. 36 is a sectional view of the vessel body and sealing member of FIG. 35, taken with an organoid present in the chamber and with the magnet replaced by a needle having a tip that has pierced the breachable barrier and entered the organoid.

FIG. 36 shows vessel 190 taken with an organoid 52 present in chamber 54, and with magnet 200 replaced by an instrument 198 structured as a needle 204 (compare with FIG. 35). A sharp tip 206 of needle 204 has pierced barrier 196 (now referred to as breached barrier 196') and has entered organoid 52. The needle may be hollow or solid. In either case, the needle may permit a sample of organoid 52 to be collected and removed from chamber 54 via access tube 192, for biopsy of the organoid. Alternatively, or in addition, the needle may be used to introduce fluid, cells, and/or effectors, among others into organoid 52 and chamber 54. For example, the needle may permit tissue or cells to be transplanted to the organoid, to achieve xenografting, allografting, or homografting.

FIG. 37 shows vessel 190 as in FIG. 36 but with instrument 198 being a sensor/electrode 208 including an electrical connector 210 (e.g., one or more electrically conductive wires). A sensing/stimulating end region 212 of sensor/electrode 208 has pierced barrier 196 (now breached barrier 196') and entered organoid 52. In other embodiments, barrier 196 may be breached first by a different instrument 198, such as a dedicated breaching instrument, and then replaced by sensor/electrode 208 (or any of the other instruments disclosed herein, among others). Sensor/electrode 208 may include at least one electrode or an array of electrodes for electrical stimulation of organoid 52. Alternatively, or in addition, sensor/electrode 208 may include any suitable sensor(s), such as an electrical sensor (e.g., a capacitance sensor), a pH sensor to measure pH, an electrochemical sensor, an oxygen sensor, a $CO_2$ sensor, and/or the like.

FIGS. 38-40 show an instrument 198 structured as a breaching instrument 214 before, during, and after barrier 196 at the bottom end of access tube 192 is pierced. In FIG. 38, a pointed tip 216 of breaching instrument 214 is traveling downward, indicated by a motion arrow at 218, and has almost reached barrier 196. In FIG. 39, tip 216 is in contact with barrier 196 and is applying a deforming force to the barrier. In FIG. 40, tip 216 has passed completely through the barrier and entered chamber 54. The wall region forming barrier 196 may be sufficiently elastic to maintain radial contact with breaching instrument 214, after the barrier has been pierced. This radial contact may form a fluid-tight seal 220 between vessel body 78 (at breached barrier 216') and breaching instrument 214, which may substantially prevent fluid in chamber 54 from traveling upward into access tube 192.

Vessel 190 may have only one or a plurality of access tubes 192. For example, FIG. 41 shows vessel 190 sectioned generally as in FIG. 24, such that three access tubes 192 are visible. Each access tube 192 may end at a respective barrier 196, as described above. Moreover, each barrier 196 may be a wall region of top wall 58 that is located intermediate, and/or shared between, the corresponding access tube 192 and chamber 54. Accordingly, the wall region may or may not be a common wall region. In the depicted embodiment, a respective breaching instrument 214 is disposed in each of the three access tubes 192, with only one of the breaching instruments extending into chamber 54. (The breached barrier is indicated with 196'.) In other embodiments, any suitable number of barriers 196 may be breached to provide access to chamber 54 with any suitable combination of instruments 198.

FIGS. 42-44 show fragmentary sectional views of a different embodiment 230 of vessel 50, taken as in FIGS. 38-40, before, during, and after barrier 196 is breached with breaching instrument 214. Barrier 196 of vessel 230 has a frangible web 232 at which the barrier is preferentially torn in response to pressure applied by breaching instrument 214. In FIG. 44, the end of breaching instrument 214 has entered chamber 54. Fluid may travel upward from chamber 54 into access tube 192, or this fluid travel may be restricted by a close radial fit of breaching instrument 214 with access tube 192 and/or a hermetic seal around the breaching instrument at the top of access tube 192, among others.

Figure 45:
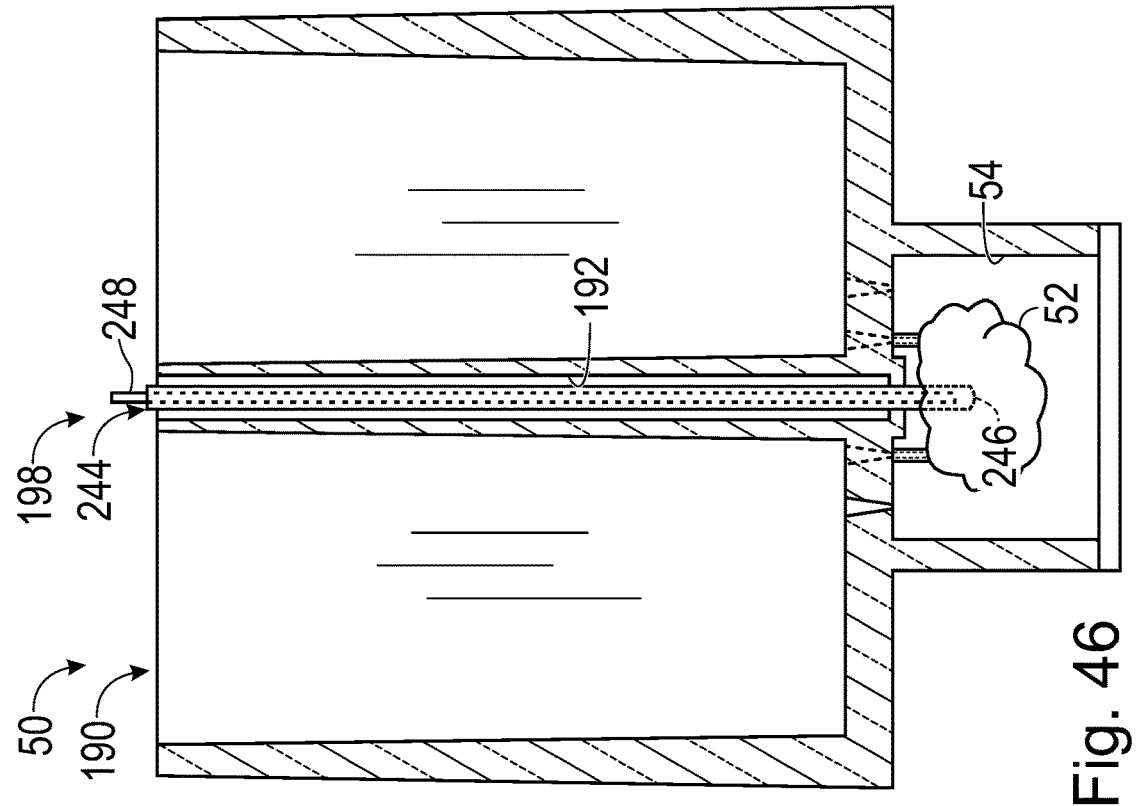
FIG. 45 is a sectional view of the vessel body and sealing member of FIG. 35, taken with an organoid present in the chamber and with the magnet replaced by an Attenuated Total Reflectance (ATR) fiberoptic probe having a tip that has pierced the breachable barrier and entered the organoid.

FIG. 45 shows vessel 190 with an Attenuated Total Reflectance (ATR) fiberoptic probe 234 disposed in access tube 192 and extending into organoid 52 in chamber 54. ATR probe 234 has an illumination fiber 236 to direct light from a light source to a bottom end of probe 234, indicated at 238, and a sensor fiber 240, to direct light from the bottom end to an optical sensor (e.g., a spectrometer, photometer, or the like), indicated at 242. Probe 234 may permit IR spectroscopy (e.g., for chemical analysis of the organoid), Raman spectroscopy (such as surface-enhanced Raman spectroscopy), or the like.

Figure 46:
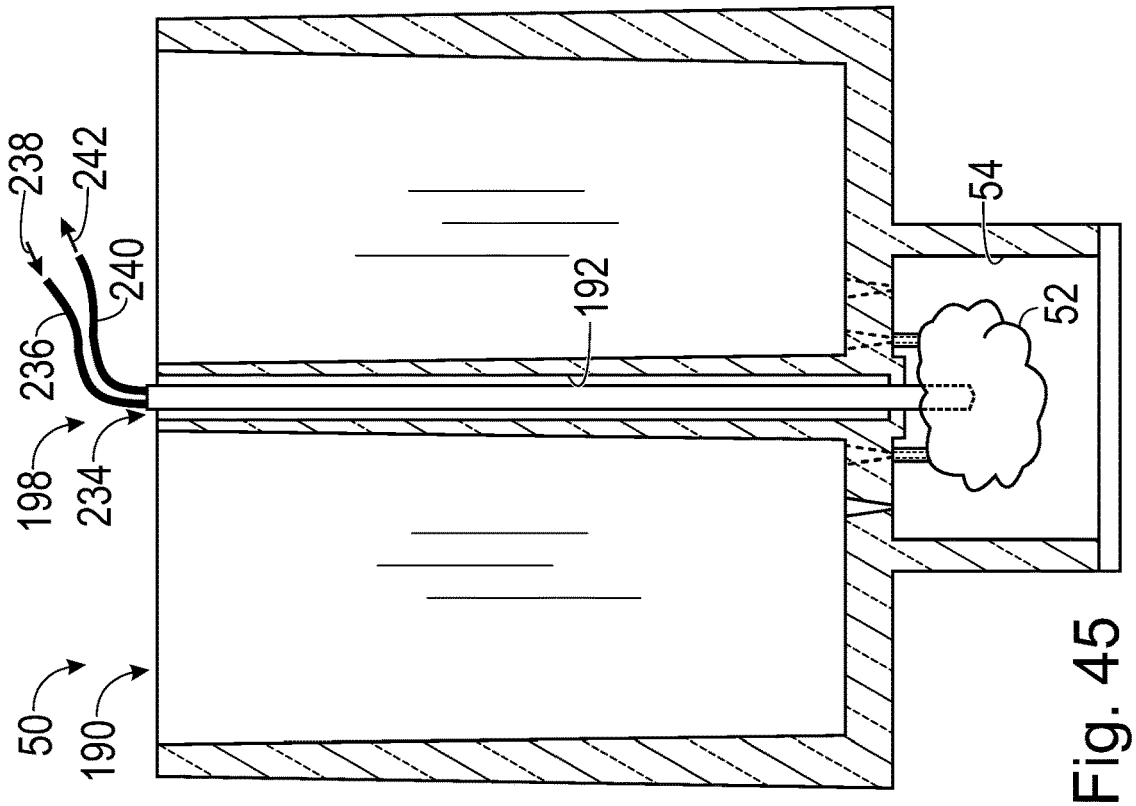
FIG. 46 is a sectional view of the vessel body and sealing member of FIG. 35, taken with an organoid present in the chamber and with the magnet replaced by an imaging fiberoptic probe having a front lens that has passed through the breachable barrier and entered the organoid.

FIG. 46 shows vessel 190 with a fiberoptic imaging probe 244 disposed in access tube 192 and extending into organoid 52 in chamber 54. Imaging probe 244 may have an endoscope front lens 246 and a fiber bundle 248 for propagation of light from front lens 246 to an image sensor. The imaging probe may permit endoscopic imaging, confocal imaging, and/or illumination only (e.g., for imaging with an image sensor not coupled to fiber bundle 248, optogenetics, etc.), among others.

Figure 47:
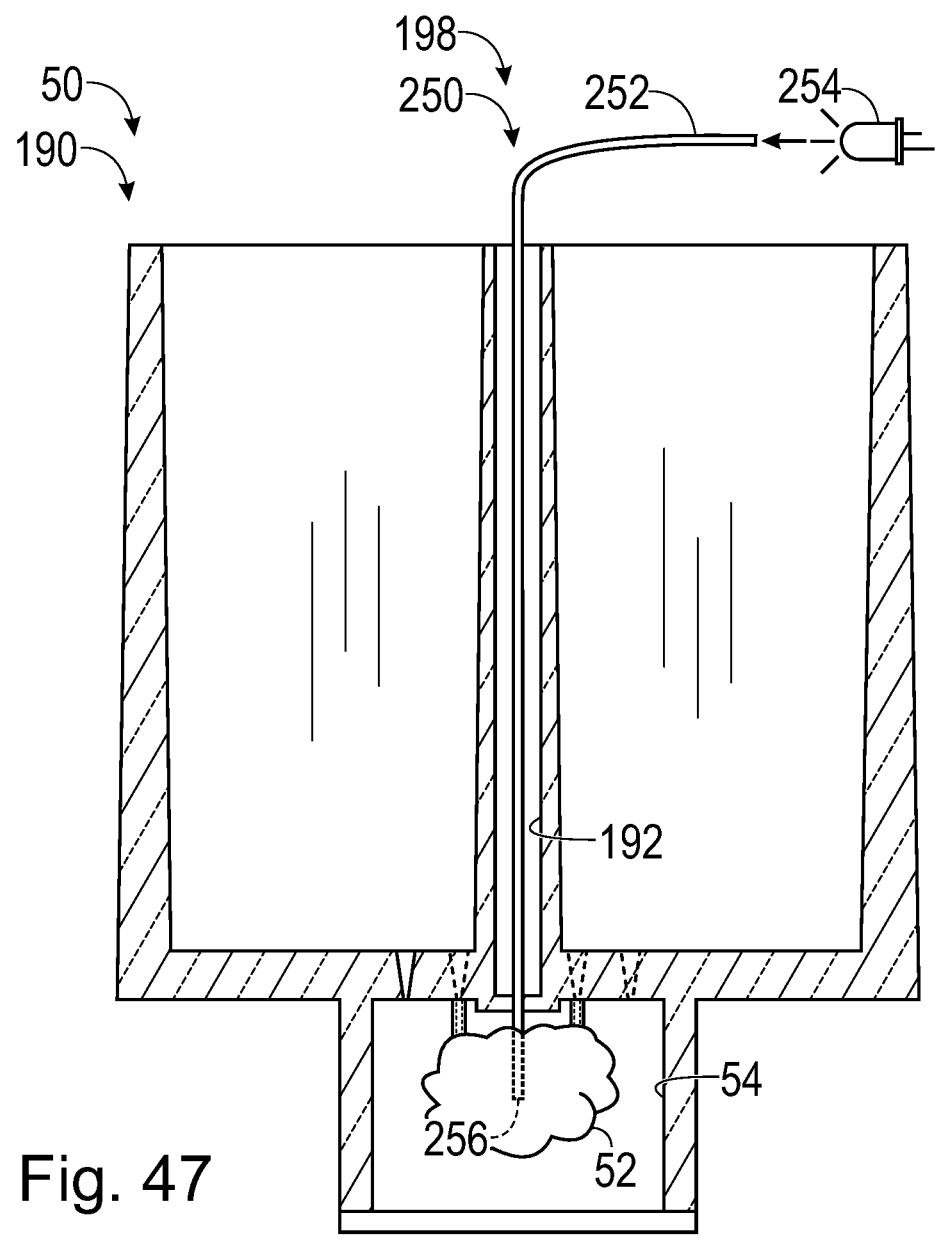
FIG. 47 is a sectional view of the vessel body and sealing member of FIG. 35, taken with an organoid present in the chamber and with the magnet replaced by an illumination probe having as distal end that has entered the organoid.

FIG. 47 shows vessel 190 with an illumination device 250 disposed in access tube 192 and extending into organoid 52 in chamber 54. Illumination device 250 may include an optical fiber 252 to direct light from a light source 254 to an outlet aperture 256 at a distal end of optical fiber 252. Exemplary uses for illumination device 250 include illuminating organoid 52 for imaging by an image sensor not coupled to optical fiber 252, as a light source for wavefront sensing (adaptive optics), as a light source for optogenetics, etc.

Figure 48:
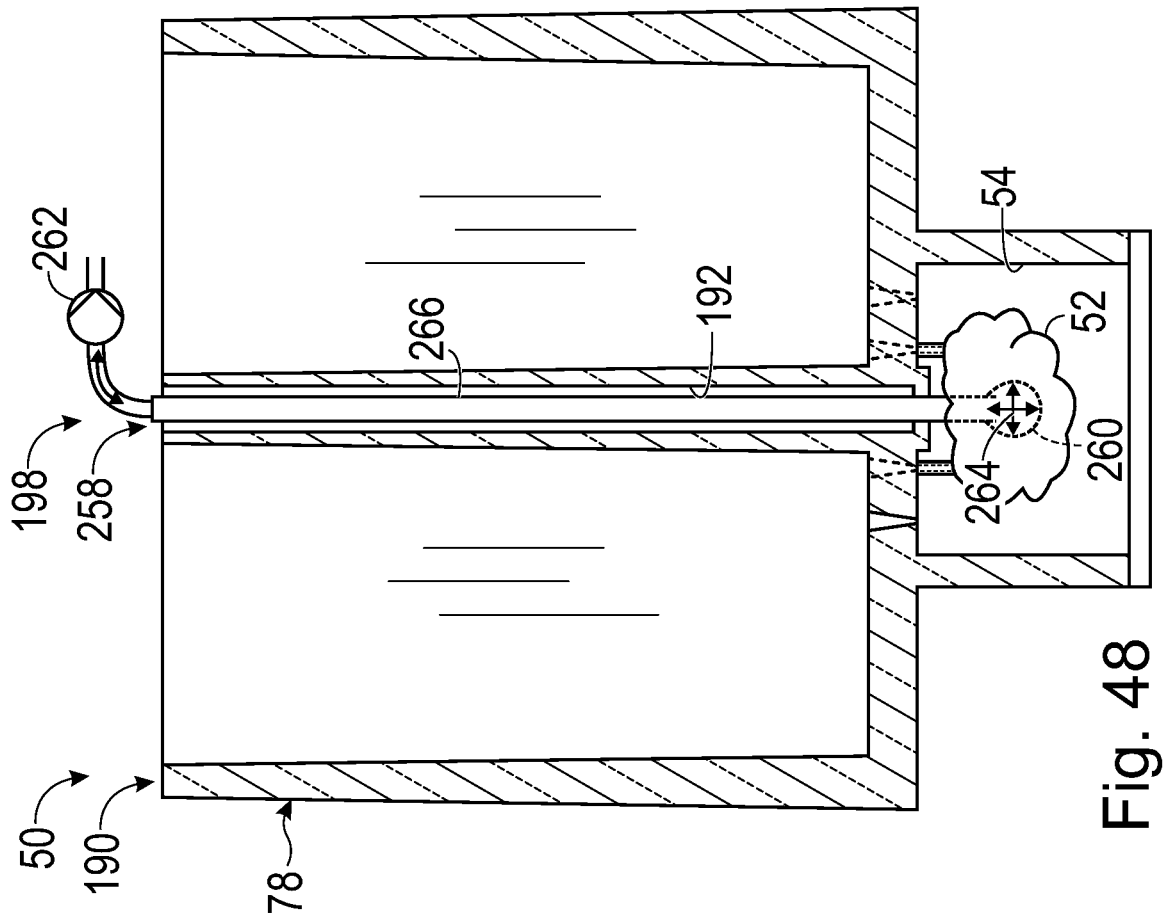
FIG. 48 is a sectional view of the vessel body and sealing member of FIG. 35, taken with an organoid present in the chamber and with the magnet replaced by a pneumatic device having an expandable balloon located inside the organoid to create internal mechanical strain.

FIG. 48 shows vessel 190 with a pneumatic device 258 located in access tube 192. Pneumatic device 258 has an expandable balloon 260 located inside organoid 52. The balloon is operatively connected to a pressure modulating device, such as a pump 262, which can inflate balloon 260 to create internal mechanical strain in organoid 52, indicated at 264. Pneumatic device 258 can inflate and deflate balloon 260, to expand and contract it as needed. Balloon 260 may be printed along with scaffold 86, and connected later to a tube 266 of pneumatic device 258. In other embodiments, balloon 260 may be introduced into organoid 52 via a needle or other sharp object.

Figure 49:
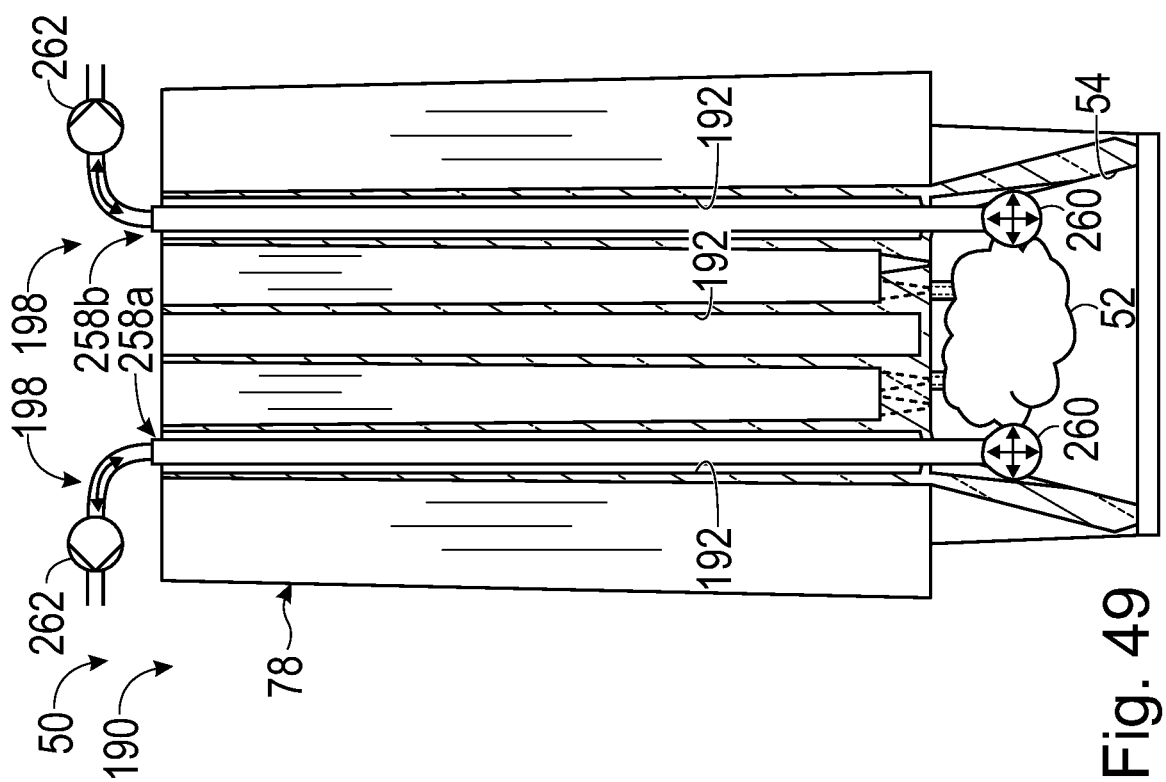
FIG. 49 is a sectional view of the vessel body and sealing member of FIG. 35, taken as in FIG. 24 (for a related embodiment) with an organoid present in the chamber and with the magnet replaced by a pair of pneumatic devices having expandable balloons located outside the organoid to create external mechanical strain.

FIG. 49 shows vessel 190 as in FIG. 41, but with a pair of pneumatic devices 258a, 258b disposed in respective access tubes 192. Each of the pneumatic devices is similar to that of FIG. 48 except for having expandable balloons 260 located outside the organoid to create external mechanical strain on opposite sides of organoid 52.

Figure 51:
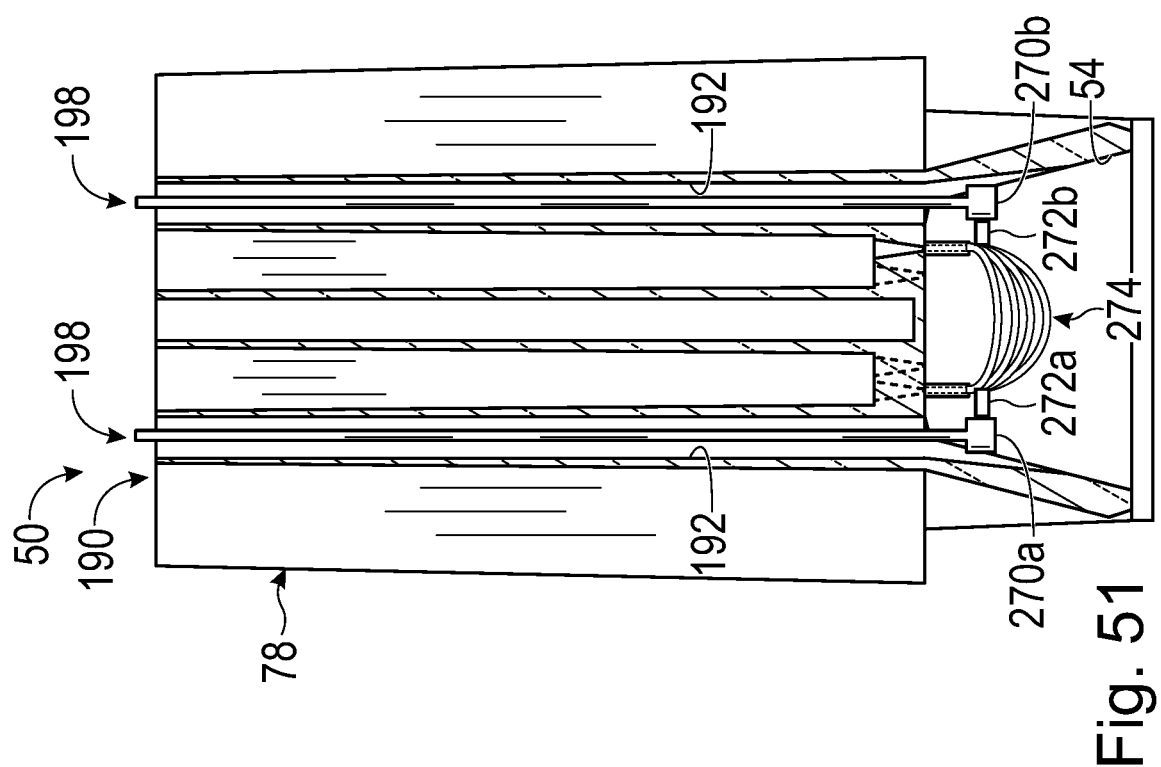
FIGS. 50 and 51 are views of the vessel body and sealing member of FIG. 35, taken generally as in FIGS. 25 and 24, respectively (for a similar embodiment), with a pair of magnets extending into the chamber via corresponding access tubes and mounting a pre-manufactured scaffold structure or biochip to the magnets via magnetic attraction.
Figure 50:
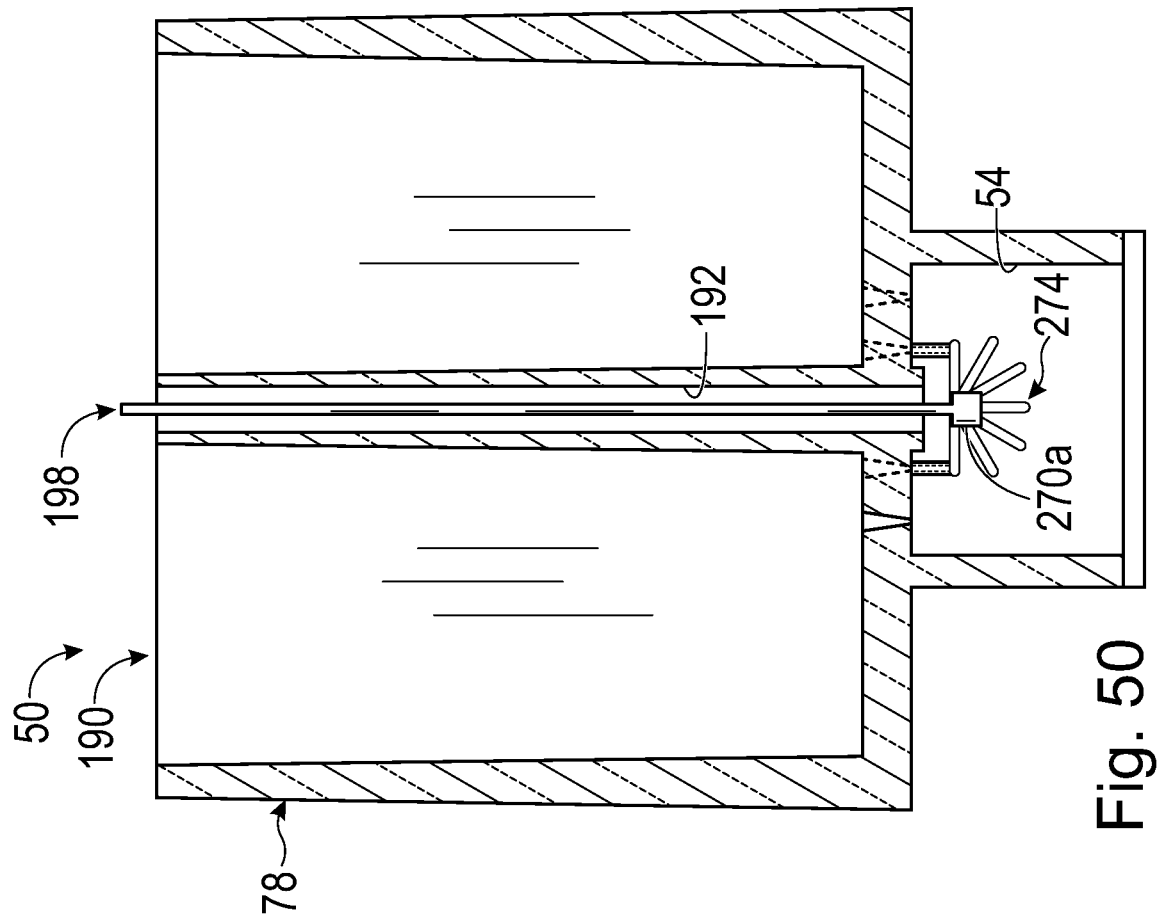

FIGS. 50 and 51 show vessel 190 viewed respectively as in FIGS. 35 and 36, but with a pair of mounting magnets 270a, 270b extending into chamber 54 via corresponding access tubes 192. Magnets 270a, 270b magnetically attract respective magnets 272a, 272b, which are already attached to a premanufactured scaffold structure 274 or biochip via magnetic attraction.

Example 8

Vessel with Flexible Membrane

This example describes an exemplary vessel 190 utilizing one or more flexible membranes (interchangeably called diaphragms) to drive fluid flow within the vessel; see FIGS. 52 and 53.

Vessel 190 includes a cap 282 mounted on the top of vessel body 78. Cap 282 forms a hermetic seal with vessel body 78. The cap includes a frame 284 that fits tightly on the top edges of vessel body 78. At least one flexible membrane 286 is mounted to frame 284 and covers at least two reservoirs (e.g., 64a, 64b). An undeformed configuration of flexible membrane is shown dashed, at 288. Pressure 290 can be applied to flexible membrane 286 over reservoir 64a or 64b to push the membrane down, indicated at 292. This pressure drives fluid from one reservoir to the other reservoir via chamber 54, indicated by arrows 294, 296. Flexible membrane 286 may deflect upward in response, indicated by 298. Pressure may be applied to flexible membrane 286 alternatively over reservoirs 64a, 64b, as shown in FIGS. 52 and 53, to drive fluid in opposite directions between the reservoirs.

Example 9

Selected Embodiments

This example describes selected embodiments of the present disclosure as a series of indexed paragraphs.

Paragraph A1. A method of organoid culture and/or analysis, the method comprising: (a) sealing an open side of a receptacle to create a chamber; and (b) forming an organoid in the chamber.

Paragraph A2. The method of paragraph A1, wherein sealing includes attaching a sealing member to the open side of the receptacle.

Paragraph A3. The method of paragraph A2, wherein attaching a sealing member includes bonding the sealing member to the receptacle.

Paragraph A4. The method of paragraph A3, wherein bonding includes bonding a pre-made sealing member to the receptacle.

Paragraph A5. The method of paragraph A2 or A3, wherein sealing includes hardening/solidifying a sealing material at least partially in the receptacle to form the sealing member.

Paragraph A6. The method of paragraph A5, wherein the sealing material includes a thermoset resin.

Paragraph A7. The method of paragraph A6, wherein sealing includes forming a layer of the thermoset resin in the receptacle, and irradiating the layer of the thermoset resin with electromagnetic radiation, such as ultraviolet light, to cure the thermoset resin.

Paragraph A8. The method of paragraph A7, wherein the receptacle contains a scaffold to promote organoid formation, and wherein irradiating is performed with a sheet of light positioned and oriented to preferentially irradiate the layer of thermoset resin relative to the scaffold.

Paragraph A9. The method of paragraph A7, wherein the receptacle contains a scaffold to promote organoid formation and also contains a light-blocking layer located intermediate the layer of the thermoset resin and the scaffold, and wherein irradiating is performed such that light propagates through the layer of the thermoset resin to the light-blocking layer, which substantially shields the scaffold from the light.

Paragraph A10. The method of any of paragraphs A7 to A9, wherein forming a layer of the thermoset resin includes depositing the thermoset resin with a 3D printer onto a hydrogel located in the receptacle.

Paragraph A11. The method of paragraph A10, wherein the hydrogel includes a scaffold to support organoid formation.

Paragraph A12. The method of paragraph A11, wherein the hydrogel includes a first hydrogel to promote organoid formation and a second hydrogel to temporarily support the layer of the thermoset resin, and wherein the second hydrogel is configured to substantially melt or dissolve when the chamber is used for organoid culture.

Paragraph A13. The method of any of paragraphs A1 to A3 and A5, wherein the receptacle contains a scaffold to promote organoid formation, and wherein sealing includes forming a layer of thermoplastic material over a hydrogel containing the scaffold, and hardening the layer of thermoplastic material by cooling to hermetically seal the open side of the receptacle.

Paragraph A14. The method of any of paragraphs A1 to A13, wherein the receptacle is defined by a vessel body, and wherein sealing includes attaching a sealing member to a bottom end of the vessel body.

Paragraph A15. The method of any of paragraphs A1 to A14, the method further comprising introducing fluid and/or at least one substance into the chamber from an overlying reservoir (for contact with the organoid), and wherein, optionally, the chamber and the overlying reservoir are formed integrally with one another.

Paragraph A16. The method of paragraph A15, wherein introducing includes passing the fluid and/or at least one substance into the chamber via a channel extending from the overlying reservoir to the chamber, and wherein, optionally, the channel is formed integrally with the overlying reservoir and the chamber.

Paragraph A17. The method of paragraph A15 or A16, wherein introducing includes passing nutrients through a top wall of the chamber to feed the organoid.

Paragraph A18. The method of any of paragraphs A15 to A17, wherein introducing includes passing a label through a top wall of the chamber to label at least a portion of the organoid.

Paragraph A19. The method of any of paragraphs A15 to A18, wherein introducing includes
(i) passing one or more effectors through a top wall of the chamber, and wherein the one or more effectors are selected from the group consisting of differentiation factors, growth factors, anti-cancer compounds, expression vectors, viruses, oligonucleotides, messenger RNAs, and small-interfering RNAs; and/or
(ii) passing molecules through a top wall of the chamber, wherein the molecules are configured for genome editing of an organoid (e.g., deletion, insertion, or substitution of one or more nucleotides of a target sequence within cells of the organoid), such as genome editing using a CRISPR-Cas system, a TALEN system, or the like; and/or
(iii) passing molecules through a top wall of the chamber to label or one or more genomic loci of an organoid in vivo and/or to alter expression of one or more genes by binding to those genes, wherein the molecules are based on a CRISPR-Cas system, a TALEN system, or the like.
The molecules of (ii) or (iii) above may include any combination of a guide RNA, an effector molecule for CRISPR-Cas expression, a virus that contains an expression vector for a guide RNA and/or a CRISPR-Cas system protein, or a CRISPR-Cas protein.

Paragraph A20. The method of any of paragraphs A15 or A19, wherein introducing includes passing one or more fixation agents and/or clearing agents through a top wall of the chamber.

Paragraph A21. The method of any of paragraphs A15 to A20, wherein introducing includes driving fluid into the chamber from the reservoir with gravity.

Paragraph A22. The method of any of paragraphs A15 to A21, wherein introducing incudes driving fluid from an inlet to an outlet of the chamber, and wherein each of the inlet and the outlet includes a respective channel that extends through a top wall of the chamber.

Paragraph A23. The method of any of paragraphs A15 to A22, wherein the chamber is in separate fluid communication with first and second overlying reservoirs, and wherein introducing includes introducing fluid and/or at least one substance into the chamber from each of the first and second overlying reservoirs.

Paragraph A24. The method of paragraph A23, wherein the organoid defines an interior space located inside the organoid and an exterior space located outside the organoid and within the chamber, and wherein fluid held by the first overlying reservoir is supplied to the interior space and fluid held by the second overlying reservoir is supplied to the exterior space.

Paragraph A25. The method of any of paragraphs A15 to A24, wherein the chamber is in separate fluid communication with first and second reservoirs, the method further comprising transferring fluid from the second reservoir to the first reservoir with a pump to promote gravity-driven flow from the first reservoir to the second reservoir via the chamber.

Paragraph A26. The method of paragraph A25, wherein the pump transfers fluid from the second reservoir to the first reservoir at a rate that substantially matches a rate of the gravity-driven flow.

Paragraph A27. The method of paragraph A26, wherein the chamber is in separate fluid communication with first and second reservoirs defined by a vessel body, the method further comprising tilting the vessel body back and forth to alternately produce gravity-driven flow from the first reservoir to the second reservoir and from the second reservoir to the first reservoir.

Paragraph A28. The method of any of paragraphs A15 to A27, wherein first and second reservoirs are in fluid communication with the chamber via respective first and second channels, wherein the first and second reservoirs are in direct fluid communication with one another via a third channel that is above and spaced from a top wall of the chamber.

Paragraph A29. The method of any of paragraphs A15 to A28, wherein a first reservoir and a second reservoir overlie the chamber and are in separate fluid communication with the chamber, the method further comprising disposing a flexible membrane over the first reservoir, and applying pressure to a top side of the flexible membrane to drive fluid from the first reservoir to the second reservoir via the chamber.

Paragraph A30. The method of paragraph A29, wherein disposing a flexible membrane includes disposing a flexible membrane over each of the first and second reservoirs, and wherein applying pressure includes alternately applying pressure to the top side of the flexible membrane over the first reservoir and to the top side of the flexible membrane over the second reservoir, to alternatively drive fluid between the first and second reservoirs in opposite directions.

Paragraph A31. The method of any of paragraphs A1 to A30, further comprising disposing a scaffold inside the receptacle before the open side of the receptacle is sealed, the scaffold being configured to promote organoid formation.

Paragraph A32. The method of paragraph A31, wherein disposing a scaffold includes creating the scaffold inside the receptacle.

Paragraph A33. The method of paragraph A31, wherein disposing a scaffold includes placing a pre-made scaffold into the receptacle.

Paragraph A34. The method of any of paragraphs A31 to A33, further comprising introducing biological cells into the receptacle before the open side of the receptacle is sealed.

Paragraph A35. The method of paragraph A34, wherein the biological cells include stem cells.

Paragraph A36. The method of paragraph A34 or A35, wherein the biological cells are introduced into the scaffold as the scaffold is being created.

Paragraph A37. The method of any of paragraphs A32 and A34 to A36, wherein creating a scaffold is performed by 3D printing.

Paragraph A38. The method of paragraph A37, wherein creating a scaffold includes 3D printing at least two different hydrogels in the receptacle.

Paragraph A39. The method of paragraph A38, wherein at least one of the hydrogels contains cells once 3D-printed, to realize an arbitrarily-shaped 3D scaffold promoting the formation of a specific organoid.

Paragraph A40. The method of any of paragraphs A31 to A39, wherein the receptacle has a wall opposite the open side, and wherein the scaffold is attached to the wall.

Paragraph A41. The method of any of paragraphs A31 to A40, further comprising introducing biological cells for forming the organoid into the chamber after the open side of the receptacle is sealed to create the chamber.

Paragraph A42. The method of any of paragraphs A31 to A41, wherein the chamber has a top wall, and wherein the organoid is supported by the top wall when formed.

Paragraph A43. The method of any of paragraphs A31 to A42, wherein the chamber is in fluid communication with a plurality of overlying reservoirs via channels, the method further comprising creating an extension of one or more of the channels by 3D printing, and, optionally, embedding the extension in a hydrogel.

Paragraph A44. The method of paragraph A43, further comprising elongating and branching each extension by 3D printing to create one or more laterally permeable tubes for supplying substances to cells inside the hydrogel.

Paragraph A45. The method of paragraph A44, further comprising supplying one or more effectors via the one or more laterally permeable tubes to establish one or more concentration gradients of the effectors inside the chamber for more controlled stem cell differentiation and organoid formation.

Paragraph A46. The method of any of paragraphs A43 to A45, further comprising incorporating polymer or metal microtubes into the hydrogel to facilitate fluid flow.

Paragraph A47. The method of any of paragraphs A1 to A46, the method further comprising collecting data related to the organoid while the organoid remains in the chamber.

Paragraph A48. The method of paragraph A47, wherein collecting data includes capturing an image of at least a portion of the organoid.

Paragraph A49. The method of paragraph A48, wherein capturing includes capturing an image by light-sheet microscopy.

Paragraph A50. The method of paragraph A48 or A49, wherein capturing includes detecting photoluminescence from the organoid.

Paragraph A51. The method of any of paragraphs A48 to A50, wherein capturing includes capturing a stack of images representing a 3D structure of at least a portion of the organoid.

Paragraph A52. The method of paragraph A51, wherein capturing includes illuminating at least a portion of the organoid via a lateral window of the chamber, and detecting optical radiation that has propagated out of the chamber via a bottom window of the chamber, or vice versa.

Paragraph A53. The method of any of paragraphs A47 to A52, wherein collecting data includes assaying fluid from the chamber or an overlying compartment for an analyte.

Paragraph A54. The method of any of paragraphs A47 to A53, wherein collecting data is performed with a sensor located at least partially inside the chamber.

Paragraph A55. The method of any of paragraphs A47 to A54, wherein collecting data includes collecting data from cells and/or fluid removed from the chamber while the bottom thereof remains sealed.

Paragraph A56. The method of paragraph A55, wherein collecting data includes forming an opening in a top wall of the chamber and removing cells and/or fluid from the chamber via the opening.

Paragraph A57. The method of any of paragraphs A1 to A56, the method further comprising creating an opening in a wall of the chamber; and inserting an end of an instrument into the chamber from the opening.

Paragraph A58. The method of paragraph A57, wherein a plurality of overlying compartments share a common wall with the chamber, and wherein the opening is created in the common wall at a bottom end of one of the overlying compartments.

Paragraph A59. The method of paragraph A58, wherein the plurality of overlying compartments includes a plurality of reservoirs and one or more access tubes, and wherein the opening is created at the bottom end of one of the access tubes.

Paragraph A60. The method of paragraph A58 or A59, wherein the opening is created with the instrument, and wherein creating an opening includes breaching the common wall with the end of the instrument.

Paragraph A61. The method of any of paragraphs A57 to A60, wherein the end of the instrument is a sharp end.

Paragraph A62. The method of paragraph A60 or A61, wherein creating an opening includes forming a fluid-tight seal between the instrument and the common wall at the opening.

Paragraph A63. The method of any of paragraphs A60 to A62, wherein the common wall defines a feature at which the common wall is configured to be torn by mechanical pressure exerted on the common wall via the instrument.

Paragraph A64. The method of any of paragraphs A57 to A63, wherein the instrument is selected from the group consisting of a needle, a light guide operatively connected to a light source, an endoscope, an electrode, an ATR probe, a source of pneumatic/hydraulic pressure optionally coupled to a balloon, and a magnet.

Paragraph A65. The method of any of paragraphs A57 to A64, wherein the instrument includes a sensor located at the end thereof.

Paragraph A66. The method of paragraph A65, further comprising sensing a parameter of the chamber and/or organoid using the sensor.

Paragraph A67. The method of any of paragraphs A57 to A66, wherein the instrument includes an electrode configured to electrically stimulate the organoid.

Paragraph A68. The method of paragraph A67, the method further comprising electrically stimulating the organoid using the electrode.

Paragraph A69. The method of any of paragraphs A57 to A68, wherein the instrument includes a light guide optically coupled to a light source and having an aperture at the end introduced into the chamber.

Paragraph A70. The method of any of paragraphs A57 to A69, wherein the instrument includes a magnet located at the end introduced into the chamber.

Paragraph A71. The method of any of paragraphs A57 to A70, wherein the instrument includes an Attenuated Total Reflectance (ATR) probe.

Paragraph A72. The method of any of paragraphs A57 to A71, wherein the instrument includes an endoscope.

Paragraph A73. The method of any of paragraphs A57 to A72, wherein the instrument is coupled to a source of pneumatic or hydraulic pressure.

Paragraph A74. The method of any of paragraphs A1 to A73, further comprising introducing a test compound into the chamber.

Paragraph A75. The method of any of paragraphs A1 to A74, wherein the method includes forming a plurality of organoids in a corresponding plurality of chambers.

Paragraph A76. The method of paragraph A75, further comprising applying a different treatment to each of the organoids.

Paragraph A77. The method of paragraph A76, wherein applying a different treatment includes introducing a different test compound into each chamber of the plurality of chambers.

Paragraph A78. The method of paragraph A77, wherein each different test compound is a potential anti-cancer drug.

Paragraph A79. The method of any of paragraphs A76 to A78, further comprising introducing one or more cells, optionally cancer cells, into each of the chambers.

Paragraph A80. The method of paragraph A79, wherein the one or more cells are introduced into the organoid in the chamber, optionally via a needle, optionally wherein the needle pierces a top wall of the chamber.

Paragraph A81. The method of any of paragraphs A76 to A80, further comprising collecting data for each organoid of the plurality of organoids to test the different treatments for an effect on the organoids.

Paragraph A82. The method of paragraph A81, wherein collecting data includes imaging each organoid in situ in its respective chamber.

Paragraph A83. The method of paragraph A81 or A82, wherein collecting data includes assaying, for an analyte, a respective fluid associated with each organoid.

Paragraph A84. The method of any of paragraphs A81 to A83, wherein collecting data includes removing each organoid from its chamber, optionally after removing the sealing member.

Paragraph A85. The method of paragraph A84, wherein collecting data includes imaging each organoid after removal from its chamber.

Paragraph A86. The method of paragraph A85, wherein collecting data includes physically sectioning each organoid after removal from its chamber; and, optionally, imaging of a plurality of sections produced by physically sectioning.

Paragraph B1. A method of organoid culture and/or analysis, the method comprising: (a) forming an organoid inside a chamber, wherein an access tube overlies the chamber, and wherein a bottom end of the access tube is closed by a top wall region of the chamber; (b) supplying nutrients to the chamber to feed the organoid; (c) forming an opening through the top wall region; and (d) inserting an end of an instrument into the chamber from the access tube.

Paragraph C1. A method of organoid culture and/or analysis, the method comprising: (a) sealing an open side of a receptacle to create a chamber; (b) forming an organoid inside the chamber; (c) supplying substances/fluid to the chamber; and (d) capturing an image of at least a portion of the organoid while the organoid remains enclosed by walls of the chamber.

Paragraph D1. A device for culture and/or analysis of an organized multi-cellular structure (e.g., an organoid), the device comprising: (a) a body defining a receptacle and at least two reservoirs, the at least two reservoirs overlying the receptacle and being in separate fluid communication with the receptacle via respective channels; and (b) a sealing member bonded or bondable to the body at an open side of the receptacle, to create a chamber for an multi-cellular structure.

Paragraph D2. The device of paragraph D1, further comprising a scaffold for biological cells attached to a wall of the receptacle.

Paragraph D3. The device of paragraph D2, wherein the scaffold is included in a hydrogel.

Paragraph D4. The device of paragraph D3, wherein the hydrogel contains biological cells.

Paragraph D5. The device of paragraph D4, wherein the biological cells include stem cells.

Paragraph D6. The device of any of paragraphs D3 to D5, wherein the hydrogel contains deposits of a drug.

Paragraph D7. The device of paragraph D6, wherein the deposits can be opened by light-induced uncaging to release the drug from the deposits.

Paragraph D8. The device of any of paragraphs D1 to D7, wherein the receptacle and the at least two reservoirs are formed integrally with one another.

Paragraph D9. The device of any of paragraphs D1 to D8, wherein the body is injection-molded as a single piece.

Paragraph D10. The device of any of paragraphs D1 to D9, wherein each reservoir of the at least two reservoirs shares a wall with the receptacle.

Paragraph D11. The device of any of paragraphs D1 to D10, wherein each channel extends through a wall that is located intermediate, and optionally shared between, the corresponding reservoir and the receptacle.

Paragraph D12. The device of any of paragraphs D1 to D11, further comprising a removable lid configured to cover an open top of each reservoir of the at least two reservoirs.

Paragraph D13. The device of any of paragraphs D1 to D12, wherein the device is in a sterilized condition.

Paragraph D14. The device of any of paragraphs D1 to D13, wherein the sealing member is bonded to the body.

Paragraph D15. The device of paragraph D14, wherein an organoid is contained in the chamber.

Paragraph D16. The device of any of paragraphs D1 to D15, wherein the body defines at least four reservoirs each disposed in fluid communication with the receptacle.

Paragraph D17. The device of any of paragraphs D1 to D16, wherein the sealing member is configured to provide a bottom window for imaging at least a portion of an organoid contained in the chamber.

Paragraph D18. The device of any of paragraphs D1 to D17, wherein the body provides a pair of lateral windows to permit illumination of at least a portion an organoid contained in the chamber via either of the lateral windows.

Paragraph D19. The device of any of paragraphs D1 to D18, wherein the body defines an access tube having an open top end and closed bottom end, and wherein a shared wall separates the chamber from the bottom end of the tube.

Paragraph D20. The device of any of paragraphs D1 to D19, further comprising a linear array of substantially identical units connected to one another, wherein one of the units includes the receptacle and the at least two reservoirs.

The term "exemplary" as used in the present disclosure, means "illustrative" or "serving as an example." Similarly, the term "exemplify" means "illustrate by giving an example." Neither term implies desirability nor superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of organoid culture, the method comprising:
   positioning a receptacle and an integrally-formed reservoir in an inverted position wherein the receptacle is disposed above the integrally-formed reservoir;
   disposing a scaffold in the receptacle through an open top;
   bonding a sealing member to the open top of the receptacle to create a chamber;
   inverting the chamber and the integrally-formed reservoir such that the chamber is disposed below the integrally-formed reservoir; and
   forming an organoid in the chamber using the scaffold.

2. The method of claim 1, wherein bonding includes bonding a pre-made sealing member to the receptacle.

3. The method of claim 1, wherein bonding includes forming the sealing member by solidifying a sealing material at least partially in the receptacle.

4. The method of claim 1, further comprising introducing fluid and/or at least one substance into the chamber from the integrally-formed reservoir when in the inverted position.

5. The method of claim 1, wherein disposing a scaffold includes 3D printing a scaffold in the receptacle.

6. The method of claim 1, further comprising capturing an image of at least a portion of the organoid while the organoid is located in the chamber.

7. The method of claim 6, wherein capturing includes capturing an image by light-sheet microscopy.

* * * * *